United States Patent
Forsberg et al.

(10) Patent No.: US 11,931,071 B2
(45) Date of Patent: Mar. 19, 2024

(54) NASAL VALVE IMPLANTS AND METHODS OF IMPLANTING THE SAME

(71) Applicant: Entellus Medical, Inc., Maple Grove, MN (US)

(72) Inventors: Andrew T. Forsberg, Plymouth, MN (US); Anthony A. Duda, Forest Lake, MN (US)

(73) Assignee: Entellus Medical, Inc., Plymouth, MN (US)

( * ) Notice: Subject to any disclaimer, the term of this patent is extended or adjusted under 35 U.S.C. 154(b) by 247 days.

(21) Appl. No.: 17/214,875

(22) Filed: Mar. 28, 2021

(65) Prior Publication Data

US 2021/0212726 A1    Jul. 15, 2021

Related U.S. Application Data

(63) Continuation of application No. 16/094,413, filed as application No. PCT/US2017/030201 on Apr. 28, 2017, now Pat. No. 10,987,133.

(Continued)

(51) Int. Cl.
*A61B 17/34*    (2006.01)
*A61B 17/064*    (2006.01)
(Continued)

(52) U.S. Cl.
CPC ........ *A61B 17/3468* (2013.01); *A61B 17/064* (2013.01); *A61B 17/24* (2013.01);
(Continued)

(58) Field of Classification Search
CPC ................ A61B 17/3468; A61B 17/24; A61B 2017/0646; A61F 2/186
See application file for complete search history.

(56) References Cited

U.S. PATENT DOCUMENTS 2,173,848 A    9/1939   Kraus
3,395,709 A    8/1968   Rubin
(Continued)

FOREIGN PATENT DOCUMENTS

CN    102770080 A    11/2012
CN    103118610       5/2013
(Continued)

OTHER PUBLICATIONS

PCT International Preliminary Report on Patentability (Chapter I of the Patent Cooperation Treaty) for PCT/US2017/030201, Applicant: Entellus Medical, Inc., Form PCT/IB/326 and 373, Docket No. ENTL-36, dated Nov. 5, 2018 (8 pages).
(Continued)

*Primary Examiner* — Thomas McEvoy
(74) *Attorney, Agent, or Firm* — McDonnell Boehnen Hulbert & Berghoff LLP

(57) ABSTRACT

A nasal valve implant delivery system includes a delivery tool having a handle and a needle extending distally therefrom and configured to hold an implant therein. When loaded in the needle, the implant proximally abuts or is disposed adjacent to a pusher member disposed partially within the needle. A light source disposed within the delivery tool is coupled to an optical fiber carried within a lumen of the pusher member. The delivery tool includes a moveable needle shuttle disposed in the handle that is coupled to the needle. An actuator disposed in the handle is configured to releaseably engage with the moveable needle shuttle, wherein the needle shuttle is coupled to one or more springs configured to apply a proximal tensioning force on the needle shuttle, wherein actuation of the actuator retracts the needle proximally into the handle and releases the implant.

20 Claims, 25 Drawing Sheets

Related U.S. Application Data

(60) Provisional application No. 62/456,427, filed on Feb. 8, 2017, provisional application No. 62/378,577, filed on Aug. 23, 2016, provisional application No. 62/330,439, filed on May 2, 2016.

(51) Int. Cl.
*A61B 17/24* (2006.01)
*A61F 2/18* (2006.01)
*A61B 17/00* (2006.01)
*A61B 90/00* (2016.01)
*A61B 90/30* (2016.01)
*A61M 25/00* (2006.01)

(52) U.S. Cl.
CPC .............. *A61B 17/34* (2013.01); *A61F 2/186* (2013.01); *A61B 2017/0053* (2013.01); *A61B 2017/0646* (2013.01); *A61B 2017/0647* (2013.01); *A61B 2090/306* (2016.02); *A61B 2090/309* (2016.02); *A61B 2090/3945* (2016.02); *A61M 25/007* (2013.01)

(56) References Cited

U.S. PATENT DOCUMENTS

| | | | |
|---|---|---|---|
| 3,716,058 A | 2/1973 | Tanner, Jr. |
| 4,265,246 A | 5/1981 | Barry |
| 4,461,281 A | 7/1984 | Carson |
| 4,645,491 A | 2/1987 | Evans |
| 4,938,234 A | 7/1990 | Capriotti |
| 5,131,382 A | 7/1992 | Meyer |
| 5,163,952 A | 11/1992 | Froix |
| 5,254,106 A | 10/1993 | Feaster |
| 5,261,916 A | 11/1993 | Engelson |
| 5,286,254 A | 2/1994 | Shapland et al. |
| 5,342,348 A | 8/1994 | Kaplan |
| 5,356,431 A | 10/1994 | Pierce |
| 5,358,522 A | 10/1994 | Montgomery et al. |
| 5,411,550 A | 5/1995 | Herweck et al. |
| 5,419,760 A | 5/1995 | Narciso |
| 5,464,450 A | 11/1995 | Buscemi et al. |
| 5,500,013 A | 3/1996 | Buscemi et al. |
| 5,531,744 A | 7/1996 | Nardella et al. |
| 5,533,440 A | 7/1996 | Sher |
| 5,545,208 A | 8/1996 | Wolff et al. |
| 5,551,954 A | 9/1996 | Buscemi et al. |
| 5,591,227 A | 1/1997 | Dinh et al. |
| 5,637,113 A | 6/1997 | Tartaglia et al. |
| 5,649,977 A | 7/1997 | Campbell |
| 5,679,400 A | 10/1997 | Tuch |
| 5,683,448 A | 11/1997 | Cragg |
| 5,730,744 A | 3/1998 | Justin et al. |
| 5,735,811 A | 4/1998 | Brisken |
| 5,749,893 A | 5/1998 | Vidal et al. |
| 5,766,237 A | 6/1998 | Cragg |
| 5,769,883 A | 6/1998 | Buscemi et al. |
| 5,785,647 A | 7/1998 | Tompkins et al. |
| 5,837,008 A | 11/1998 | Berg et al. |
| 5,843,172 A | 12/1998 | Yan |
| 5,891,108 A | 4/1999 | Leone et al. |
| 5,893,840 A | 4/1999 | Hull et al. |
| 5,897,523 A | 4/1999 | Wright et al. |
| 5,951,586 A | 9/1999 | Berg et al. |
| 5,972,027 A | 10/1999 | Johnson |
| 5,980,551 A | 11/1999 | Summers et al. |
| 5,980,564 A | 11/1999 | Stinson |
| 5,980,566 A | 11/1999 | Alt et al. |
| 6,010,054 A | 1/2000 | Johnson et al. |
| 6,063,101 A | 5/2000 | Jacobsen et al. |
| 6,071,305 A | 6/2000 | Brown et al. |
| 6,099,561 A | 8/2000 | Alt |
| 6,106,541 A | 8/2000 | Herbis |
| 6,165,210 A | 12/2000 | Lau et al. |
| 6,183,433 B1 | 2/2001 | Bays |
| 6,238,411 B1 | 5/2001 | Thorner |
| 6,241,747 B1 | 6/2001 | Ruff |
| 6,241,762 B1 | 6/2001 | Shanley |
| 6,250,307 B1 | 6/2001 | Conrad et al. |
| 6,258,056 B1 | 7/2001 | Turley et al. |
| 6,268,405 B1 | 7/2001 | Yao et al. |
| 6,290,673 B1 | 9/2001 | Shanley |
| 6,293,967 B1 | 9/2001 | Shanley |
| 6,322,590 B1 | 11/2001 | Sillers et al. |
| 6,325,781 B1 * | 12/2001 | Takagi ............. A61M 25/0631 |
| | | | 604/164.08 |
| 6,390,096 B1 | 5/2002 | Conrad et al. |
| 6,401,717 B1 | 6/2002 | Conrad et al. |
| 6,415,796 B1 | 7/2002 | Conrad et al. |
| 6,431,174 B1 | 8/2002 | Knudson et al. |
| 6,450,169 B1 | 9/2002 | Conrad et al. |
| 6,454,803 B1 | 9/2002 | Romo |
| 6,516,806 B2 | 2/2003 | Knudson et al. |
| 6,656,195 B2 | 12/2003 | Peters et al. |
| 6,878,165 B2 | 4/2005 | Makino |
| 6,899,105 B2 | 5/2005 | Krueger et al. |
| 6,978,781 B1 | 12/2005 | Jordan |
| 6,982,359 B1 | 1/2006 | Beaudry |
| 7,055,523 B1 | 6/2006 | Brown |
| 7,114,495 B2 | 10/2006 | Lockwood |
| D536,792 S | 2/2007 | Krueger et al. |
| 7,213,599 B2 | 5/2007 | Conrad et al. |
| 7,237,554 B2 | 7/2007 | Conrad et al. |
| 7,322,356 B2 | 1/2008 | Critzer et al. |
| 7,322,993 B2 | 1/2008 | Metzger et al. |
| 7,337,781 B2 | 3/2008 | Vassallo |
| 7,381,222 B2 | 6/2008 | Pflueger et al. |
| 7,396,232 B2 | 7/2008 | Fromovich et al. |
| 7,419,497 B2 | 9/2008 | Muni et al. |
| 7,520,876 B2 | 4/2009 | Ressemann et al. |
| 7,563,267 B2 | 7/2009 | Goldfarb et al. |
| 7,666,203 B2 | 2/2010 | Chanduszko et al. |
| 7,678,099 B2 | 3/2010 | Ressemann et al. |
| 7,762,940 B2 | 7/2010 | Henderson et al. |
| 7,780,730 B2 | 8/2010 | Saidi |
| 7,842,062 B2 | 11/2010 | Keith et al. |
| 7,879,061 B2 | 2/2011 | Keith et al. |
| 7,905,889 B2 | 3/2011 | Catanese, III et al. |
| 7,918,871 B2 | 4/2011 | Truitt et al. |
| 7,992,566 B2 | 8/2011 | Pflueger et al. |
| 8,104,478 B2 | 1/2012 | Pflueger et al. |
| 8,133,276 B2 | 3/2012 | Saidi |
| 8,167,787 B2 | 5/2012 | Gillis |
| 8,241,266 B2 | 8/2012 | Keith et al. |
| 8,267,962 B2 | 9/2012 | Stupak |
| 8,277,478 B2 | 10/2012 | Drontle et al. |
| 8,282,667 B2 | 10/2012 | Drontle et al. |
| 8,348,969 B2 | 1/2013 | Keith et al. |
| 8,409,250 B2 | 4/2013 | Schmieding et al. |
| 8,568,439 B2 | 10/2013 | Keith et al. |
| 8,585,728 B2 | 11/2013 | Keith et al. |
| 8,585,729 B2 | 11/2013 | Keith et al. |
| 8,623,043 B1 | 1/2014 | Keith et al. |
| 8,657,846 B2 | 2/2014 | Keith et al. |
| 8,678,008 B2 | 3/2014 | Rousseau et al. |
| 8,784,488 B2 | 7/2014 | Saidi |
| 8,801,670 B2 | 8/2014 | Drontle et al. |
| 8,834,513 B2 | 9/2014 | Hanson et al. |
| 8,882,795 B2 | 11/2014 | Drontle et al. |
| 8,888,686 B2 | 11/2014 | Drontle et al. |
| 8,915,938 B2 | 12/2014 | Keith et al. |
| 8,944,990 B2 | 2/2015 | Hamel et al. |
| 9,005,284 B2 | 4/2015 | Ressemann |
| 9,101,739 B2 | 8/2015 | Lesch, Jr. et al. |
| 9,192,748 B2 | 11/2015 | Ressemann et al. |
| 9,278,199 B2 | 3/2016 | Keith et al. |
| 9,282,986 B2 | 3/2016 | Hanson et al. |
| 9,283,360 B2 | 3/2016 | Lesch et al. |
| 9,320,876 B2 | 4/2016 | Ressemann et al. |
| 9,333,327 B2 | 5/2016 | Setliff, III et al. |
| 9,339,637 B2 | 5/2016 | Drontle et al. |
| 9,370,650 B2 | 6/2016 | Hanson et al. |
| 9,433,343 B2 | 9/2016 | Drontle et al. |
| 9,440,049 B2 | 9/2016 | Drontle et al. |

(56) References Cited

U.S. PATENT DOCUMENTS

| | | | |
|---|---|---|---|
| 9,480,594 | B2 | 11/2016 | Saidi et al. |
| 9,486,614 | B2 | 11/2016 | Drontle et al. |
| 9,550,049 | B2 | 1/2017 | Hanson et al. |
| 9,597,220 | B2 | 3/2017 | Gonzales et al. |
| 9,694,167 | B2 | 7/2017 | Keith et al. |
| 9,700,705 | B2 | 7/2017 | Lesch, Jr. et al. |
| 9,775,975 | B2 | 10/2017 | Ressemann et al. |
| 10,022,525 | B2 | 7/2018 | Hanson et al. |
| 10,029,069 | B2 | 7/2018 | Keith et al. |
| 10,045,842 | B2 | 8/2018 | Alexander et al. |
| 10,086,181 | B2 | 10/2018 | Lesch et al. |
| 10,492,670 | B1 | 12/2019 | Bendory et al. |
| 2002/0019670 | A1 | 2/2002 | Crawley et al. |
| 2002/0045843 | A1* | 4/2002 | Barker ............ A61M 25/09041 604/110 |
| 2002/0173848 | A1 | 11/2002 | Sachs |
| 2003/0028076 | A1 | 2/2003 | Kuyava et al. |
| 2003/0149447 | A1 | 8/2003 | Morency et al. |
| 2003/0199970 | A1 | 10/2003 | Shanley |
| 2004/0098098 | A1 | 5/2004 | McGuckin et al. |
| 2005/0004417 | A1 | 1/2005 | Nelson et al. |
| 2005/0142162 | A1 | 6/2005 | Hunter et al. |
| 2005/0154412 | A1 | 7/2005 | Krueger et al. |
| 2006/0085027 | A1 | 4/2006 | Santin et al. |
| 2006/0147492 | A1 | 7/2006 | Hunter et al. |
| 2006/0184224 | A1 | 8/2006 | Angel |
| 2006/0185680 | A1 | 8/2006 | Bhat et al. |
| 2006/0241650 | A1 | 10/2006 | Weber et al. |
| 2006/0276817 | A1 | 12/2006 | Vassallo et al. |
| 2007/0088272 | A1* | 4/2007 | Jones ................ A61M 25/0637 604/192 |
| 2007/0173848 | A1 | 7/2007 | Lennox et al. |
| 2007/0219575 | A1 | 9/2007 | Mejia |
| 2007/0250105 | A1 | 10/2007 | Ressemann et al. |
| 2007/0250118 | A1 | 10/2007 | Masini |
| 2007/0277831 | A1 | 12/2007 | Luhrs |
| 2007/0293946 | A1 | 12/2007 | Gonzales et al. |
| 2008/0021495 | A1 | 1/2008 | Lee et al. |
| 2008/0023012 | A1 | 1/2008 | Dineen et al. |
| 2008/0027480 | A1 | 1/2008 | Van Der Burg et al. |
| 2008/0066794 | A1 | 3/2008 | Durfee |
| 2008/0077240 | A1 | 3/2008 | Saidi |
| 2008/0097335 | A1 | 4/2008 | Trogden et al. |
| 2008/0167628 | A1 | 7/2008 | Li et al. |
| 2008/0172033 | A1 | 7/2008 | Keith et al. |
| 2008/0208265 | A1 | 8/2008 | Frazier et al. |
| 2008/0234818 | A1 | 9/2008 | Kang et al. |
| 2008/0312688 | A1 | 12/2008 | Nawrocki et al. |
| 2009/0024133 | A1 | 1/2009 | Keady et al. |
| 2009/0024227 | A1 | 1/2009 | Lesh |
| 2009/0099577 | A1 | 4/2009 | Gonzales et al. |
| 2009/0198216 | A1 | 8/2009 | Muni et al. |
| 2009/0204130 | A1 | 8/2009 | Kantsevoy et al. |
| 2009/0274743 | A1 | 11/2009 | Edelman et al. |
| 2009/0312791 | A1 | 12/2009 | Lindh, Sr. et al. |
| 2009/0318875 | A1 | 12/2009 | Friedman |
| 2010/0106255 | A1 | 4/2010 | Dubin |
| 2010/0174138 | A1 | 7/2010 | Chang et al. |
| 2010/0280611 | A1 | 11/2010 | Saidi |
| 2011/0009872 | A1 | 1/2011 | Mistry et al. |
| 2011/0251634 | A1 | 10/2011 | Gonzales et al. |
| 2011/0264138 | A1 | 10/2011 | Avelar et al. |
| 2012/0053404 | A1 | 3/2012 | Schreck et al. |
| 2012/0078367 | A1 | 3/2012 | Hristov et al. |
| 2012/0215307 | A1 | 8/2012 | Chen et al. |
| 2012/0310280 | A1 | 12/2012 | Harrington |
| 2012/0323227 | A1 | 12/2012 | Wolf et al. |
| 2012/0323232 | A1 | 12/2012 | Wolf et al. |
| 2013/0096382 | A1 | 4/2013 | Alexander et al. |
| 2013/0197303 | A1 | 8/2013 | Chun et al. |
| 2013/0217958 | A1 | 8/2013 | Mujwid et al. |
| 2013/0327333 | A1 | 12/2013 | Ng et al. |
| 2014/0000631 | A1 | 1/2014 | Gillis et al. |
| 2014/0188158 | A1 | 7/2014 | Servell et al. |
| 2014/0243975 | A1 | 8/2014 | Saidi et al. |
| 2014/0277429 | A1 | 9/2014 | Kuzma et al. |
| 2014/0357959 | A1 | 12/2014 | Hanson et al. |
| 2015/0012090 | A1 | 1/2015 | Saidi |
| 2015/0032028 | A1 | 1/2015 | Rampersaud et al. |
| 2015/0051449 | A1 | 2/2015 | Qiu |
| 2015/0066071 | A1 | 3/2015 | Alexander et al. |
| 2015/0148612 | A1 | 5/2015 | Schaeffer et al. |
| 2015/0148902 | A1 | 5/2015 | Komrit |
| 2015/0196193 | A1 | 7/2015 | Kienzle et al. |
| 2015/0238363 | A1 | 8/2015 | Tan et al. |
| 2016/0058556 | A1 | 3/2016 | Rosenthal et al. |
| 2016/0151614 | A1 | 6/2016 | Ressemann et al. |
| 2016/0367286 | A1 | 12/2016 | Drontle et al. |
| 2017/0007282 | A1 | 1/2017 | Drontle |
| 2017/0028112 | A1 | 2/2017 | Drontle et al. |
| 2017/0050001 | A1 | 2/2017 | Drontle et al. |
| 2017/0079774 | A1 | 3/2017 | Saidi et al. |
| 2017/0105836 | A1 | 4/2017 | Baron et al. |
| 2017/0113027 | A1 | 4/2017 | Drontle et al. |
| 2017/0143532 | A1 | 5/2017 | Gonzales et al. |
| 2017/0368319 | A1 | 12/2017 | Lesch, Jr. et al. |
| 2018/0008806 | A1 | 1/2018 | Ressemann et al. |
| 2018/0304051 | A1 | 10/2018 | Keith et al. |
| 2018/0304058 | A1 | 10/2018 | Hanson et al. |

FOREIGN PATENT DOCUMENTS

| | | |
|---|---|---|
| EP | 1216013 B1 | 6/2006 |
| EP | 1857078 A | 11/2007 |
| EP | 147505681 B1 | 10/2010 |
| EP | 1940320 B1 | 12/2010 |
| EP | 2692313 A | 2/2014 |
| EP | 2961350 B1 | 3/2018 |
| EP | 3400906 A1 | 11/2018 |
| NO | 2003/015664 A1 | 2/2003 |
| WO | 01/01957 A1 | 12/2000 |
| WO | 01/19301 A1 | 3/2001 |
| WO | 01/21247 A1 | 3/2001 |
| WO | 2002/076354 A1 | 10/2002 |
| WO | 2003/041612 A2 | 5/2003 |
| WO | 2006/093533 A1 | 9/2006 |
| WO | 2006/101610 A2 | 9/2006 |
| WO | 2006/107957 A2 | 10/2006 |
| WO | 2007/011994 A2 | 1/2007 |
| WO | 2007/134005 A1 | 11/2007 |
| WO | 2007/134215 A2 | 11/2007 |
| WO | 2007/076493 A1 | 12/2007 |
| WO | 2008/042058 A1 | 4/2008 |
| WO | 2009/036290 A1 | 3/2009 |
| WO | 2010/033682 A1 | 3/2010 |
| WO | 2010/051273 A1 | 5/2010 |
| WO | 2010/059586 A1 | 5/2010 |
| WO | 2010/132648 A1 | 11/2010 |
| WO | 2011/082350 | 7/2011 |
| WO | 2011/092161 A1 | 8/2011 |
| WO | 2012/030673 A1 | 3/2012 |
| WO | 2012/112967 A1 | 8/2012 |
| WO | 2014/004231 A1 | 1/2014 |
| WO | 2017/192394 A1 | 11/2017 |
| WO | 2018/053297 A1 | 3/2018 |
| WO | 2018/183561 A1 | 10/2018 |

OTHER PUBLICATIONS

PCT International Search Report for PCT/US2017/030201, Applicant: Entellus Medical Inc., Form PCT/ISA/210 and 220, Docket No. ENTL-036, dated Jul. 19, 2017 (4 pages).

PCT Written Opinion of the International Search Authority for PCT/US2017/030201, Applicant: Entellus Medical Inc., Form PCT/ISA/237, Docket No. ENTL-036 dated Jul. 19, 2017 (6 pages).

The extended European search report dated Oct. 11, 2018 in European Patent Application No. 18156136.6, Applicant: Spriox, Inc., Docket No. SPRX-011 EPD IV (7 pages).

The extended European search report dated Oct. 19, 2016 in European Patent Application No. 14756699.6, Applicant: Spriox, Inc., Docket No. SPRX-011EP (7 pages).

(56) References Cited

OTHER PUBLICATIONS

Communication pursuant to Rules 70(2) and 70a(2) EPC dated Nov. 7, 2016 in European Patent Application No. 14756699.6, Applicant: Spriox, Inc., Docket No. SPRX-011 EP (1 page).
Response to Search Opinion under Rules 70(2) and 70a(2) EPC dated May 16, 2017 in European Patent Application No. 14756699.6, Applicant: Spriox, Inc., Docket No. SPRX-011 EP (26 pages).
Communication under Rule 71(3) EPC dated Oct. 18, 2017 European Patent Application No. 14756699.6, Applicant: Spriox, Inc., Docket No. SPRX-011 EP (5 pages).
Notification of Reason(s) for Refusal dated Apr. 18, 2017 in Japanese Patent Application No. JP 2015-560308, Docket No. SPRX-011JP (19 pages).
Notification of Reason(s) for Refusal dated Dec. 19, 2017 in Japanese Patent Application No. JP 2015-560308, Docket No. SPRX-011JP (10 pages).
Notification of Reason(s) for Refusal dated Jun. 26, 2018 in Japanese Patent Application No. JP 2015-560308, Dockel No. SPRX-011JP (10 pages).
Decision to Grant a Patent dated Aug. 28, 2018 in Japanese Patent Application No. JP 2015-560308, Docket No. SPRX-011JP (3 pages).
Decision on Appeal dated Oct. 26, 2018 in U.S. Appl. No. 14/331,805, Inventor(s): Iyad S. Saidi, Docket No. SPRX-001.4 (12 pages).
Kim et al.; Analysis of cartilage-polydioxanone foil composite grafts; Facial Plast. Surg.; 29(6); pp. 502-505; doi:10.1055/s-0033-1360593; (Author Manuscript); Dec. 2013.
Parylene Engineering; Why use parylene; retrieved from the Internet (http://www.paryleneengineering.com/why_use_parylene_htm); 3 pages; on Oct. 2, 2017.
Cole; Biophysics of nasal air flow: A review; American Journal of Rhinology; 14(4); pp. 245-249; Jul./Aug. 2000.
Cole; The four components of the nasal valve; American Journal of Rhinology; 17(2); pp. 107-110; Mar./Apr. 2003.
De Pochat et al.; The role of septal cartilage in rhinoplasty: Cadaveric analysis and assessment of graft selection; Aesthetic Surgery Journal; 31 (8); pp. 891-896; Nov. 2011.
Fanous et al.; Collapsed nasal-valve widening by composite grafting to the nasal floor; Journal of Otolaryngology; 25 (5); pp. 313-316; Oct. 1996.
Friedman et al.; A simplified technique for airway correction at the nasal valve area; Otolaryngol Head Neck Surg; 131(4); pp. 519-524; Oct. 2004.
Friedman et al.; Nasal Valve Suspension: An Improved, Simplified Technique for Nasal Valve Collapse; Laryngoscope; 113(2); pp. 381-385; Jan. 2003.
Kalan et al.; Treatment of external nasal valve (alar rim) collapse with an alar strut; Journal of Laryngology and Otology; 115(10); pp. 788-791; Oct. 2001.
Karen et al.; The use of percutaneous sutures for graft fixation in rhinoplasty; Archives Facial Plastic Surgery; 5(2); pp. 193-196; Mar.-Apr. 2003.
Lambert et al; A new method for arterial drug delivery via removable stent (abstract); JACC; 21(2); p. 483A; Abstract No. 834-2; Feb. 1993.
Millman; Alar Batten grafting for management of collapsed nasal valve; Laryngoscope; 112(3); pp. 574-579; Mar. 2002.
Rhee et al.; Nasal valve surgery improves disease-specific quality of life; Laryngoscope; 115(3); pp. 437-440; Mar. 2005.
Westreich et al.; Defining nasal cartilage elasticity: Biomechanical testing of the tripod theory based on a cantilevered model; Arch Facial Plast Surg; 9(4); pp. 264-270; Jul./Aug. 2007.
English Translation of Abstract of Chinese Patent Application No. CN 102770080 dated Feb. 9, 2022.

\* cited by examiner

NASAL VALVE IMPLANTS AND METHODS OF IMPLANTING THE SAME

RELATED APPLICATIONS

This application is a continuation of U.S. patent application Ser. No. 16/094,413, filed Oct. 17, 2018, which is a national phase filing under 35 U.S.C. § 371 of International Patent Application No. PCT/US2017/030201, which claims priority to U.S. Provisional Patent Application No. 62/330,439 filed May 2, 2016, U.S. Provisional Patent Application No. 62/378,577 filed on Aug. 23, 2016, U.S. Provisional Patent Application No. 62/417,210 filed on Nov. 3, 2016, and U.S. Provisional Patent Application No. 62/456,427 filed on Feb. 8, 2017, which are hereby incorporated by reference in their entirety.

TECHNICAL FIELD

The technical field generally relates to nasal valve implants and methods of implanting the same in mammals.

BACKGROUND

The nasal valve area of a mammal is a narrow portion of the nasal passage where most flow resistance is created during breathing. It is generally the area located between the nasal septum and the lateral or mobile side of the cartilage of the nose. During inhalation when air passes through the nasal valve area, a negative pressure is formed and the valve area tends to collapse resulting in the condition known medically as vestibular stenosis. Collapse of the nasal valve area can be dynamic (for example, during exercise) or it may be fixed or permanent. There are several causes of nasal valve collapse including, for example, aging, trauma, or congenital conditions. Surgical intervention can be performed to alter the nasal valve area which places a spreader graft between the septum and the cartilage. Alternatively, prosthetic splints may be placed on the exterior of the nose (e.g., BREATHE RIGHT® strips) to aid in keeping the nasal valve area open. In still another alternative, stent-like structures can be placed inside the nose to reinforce and hold open the nasal valve area. Unfortunately, these less invasive solutions may be uncomfortable to wear and are not generally perceived as acceptable solutions for social situations.

A more recent option for addressing the collapse of the nasal valve area has been the development of stiffening implants that are inserted into the lateral cartilage of the subject and engage with or overlay the bony tissue in the upper region of the nose. Examples of these types of devices may be seen, for example, in U.S. Patent Application Publication Nos. 2011/0251634, 2014/0243975, 2016/0058556, and U.S. Pat. No. 7,780,730. The procedure used to place these stiffening implants involves pushing a sharp tool (e.g., needle) in the direction towards the eye and other structures. It is thus very important to the physician to have a very detailed understanding of the location and trajectory of the implant and/or tool tip. Existing implantation tools use external fixturing and measuring tools to determine the location of the tip of the implant and/or delivery system. These tools, however, are complex and cumbersome to use and may only give the user an approximation or estimate as to the location of the implant and tool tip. Thus, there is a need for devices and methods that aid the physician in safely placing implants in the nasal valve area.

SUMMARY

The present invention relates to nasal valve implant systems and devices as well as methods of implanting the same in mammals. In one embodiment of the invention, nasal valve implants are implanted using transillumination. According to one embodiment, a delivery tool with transillumination functionality is advanced through the nasal tissue to the desired location for delivery and implantation into the nasal valve area. Transillumination may occur through the delivery tool, the implant, or both.

In one embodiment, a method of delivering an implant into a nasal valve area of a subject includes the steps of providing a delivery tool having a distal region terminating in a distal tip, wherein at least one of the distal tip and distal region emits light therefrom. The delivery tool is advanced through nasal tissue to a desired location in the nasal valve area while light is emitted from the delivery tool, wherein the light is observable through skin of the subject (i.e., transillumination). The implant is then delivered using the delivery tool to the nasal valve area.

In another embodiment, a delivery system for delivering an implant into a nasal valve area of a subject includes a delivery tool having a distal region terminating in a distal tip. A light source is disposed within or connected to the delivery tool, wherein at least one of the distal tip and distal region emits light therefrom. An implant is disposed on or within the distal region of the delivery tool and can be delivered to the desired location into the nasal valve area.

In another embodiment, a method of delivering an implant into a nasal valve area of a subject includes providing a delivery tool having a handle and a needle extending from a distal end of the handle, wherein the implant is contained in the needle and proximally abuts or is disposed adjacent to a pusher member disposed at least partially within the needle and containing a light fiber. The delivery tool is advanced through nasal tissue to a desired location in the nasal valve area while light is emitted from the needle, wherein the light is observable by the operator of the delivery tool through skin of the subject. The implant is then delivered using the delivery tool to the nasal valve area of the subject.

In another embodiment, a delivery system for delivering an implant into a nasal valve area of a subject includes a delivery tool having a handle and a needle extending from a distal end of the handle. The implant is contained in the needle and proximally abuts or is disposed adjacent to a pusher member disposed at least partially within the needle, wherein the needle has a plurality of apertures formed therein. A light source is disposed within the delivery tool and is coupled to a light fiber terminating at the end of the pusher member. The delivery tool includes a slidable button disposed in the handle and configured to retract the needle proximally to release the implant from the needle.

In another embodiment, a delivery system for delivering an implant into a nasal valve area of a subject includes a delivery tool having a handle and a needle extending from a distal end of the handle, wherein the implant is contained in the needle and proximally abuts or is disposed adjacent to a pusher member disposed partially within the needle. The needle has a plurality of apertures formed therein. A light source is disposed within the delivery tool and is coupled to a light fiber terminating at one end of the pusher member. At least one biasing spring is disposed in the handle and is operatively coupled to the needle to apply a proximal force on the needle when the spring is in a loaded state. The handle further includes a release mechanism disposed in the handle and configured to retract the needle proximally into the handle and release the implant upon actuation. The release mechanism may include a button actuated latch, pawl, or temporary locking interface (e.g., friction engagement) that interfaces with the needle directly or an indirect slide member that is coupled to the needle. The button located on the handle is used, in one embodiment, to actuate the release mechanism.

BRIEF DESCRIPTION OF THE DRAWINGS

The drawings illustrate generally, by way of example, but not by way of limitation, various embodiments discussed in the present document.

DETAILED DESCRIPTION OF THE ILLUSTRATED EMBODIMENTS

Figure 1A:
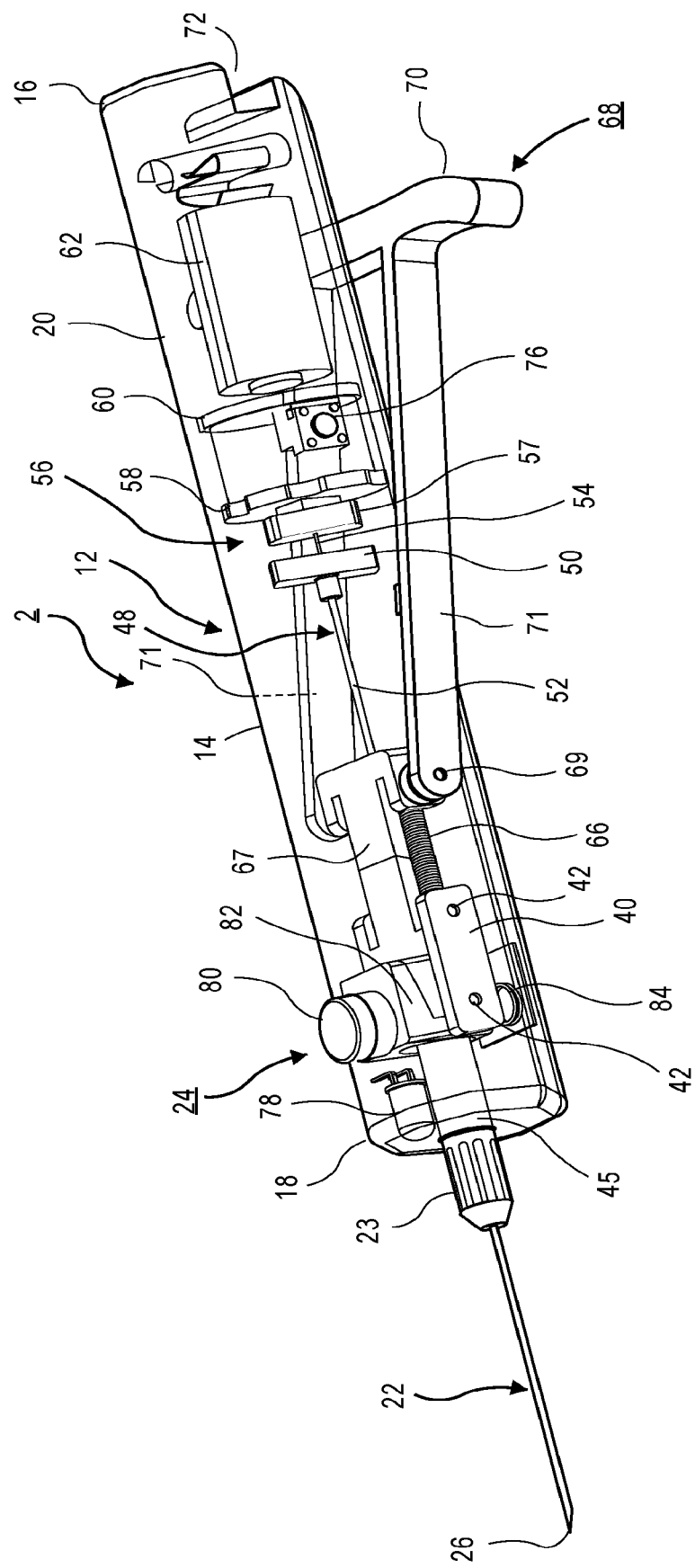
FIG. 1A illustrates a perspective view of a delivery system according to one embodiment. The arming lever is in the un-armed or shipping position where there is no tension placed on the needle shuttle springs.

The present invention relates to nasal valve implants and methods of implanting the same in mammals.

FIGS. 1A, 1B, 2A, 2B, 3A, 3B illustrate one exemplary embodiment of a delivery system 2 for delivering an implant 10 (best seen in FIG. 5) into a nasal valve area of a subject. In this embodiment, the delivery system 2 includes a delivery tool 12 that is manipulated by a user to deliver the implant to the nasal valve area of the subject. The delivery tool 12 includes a housing 14 having a proximal end 16 and a distal end 18. The external body of the housing 14 defines a handle 20 that is held or grasped by the user of the delivery tool 12 as explained herein. The handle 20 may be ergonomically designed to accommodate being held by a single hand of the user or operator. This may include various surface features such as ridges, divots, curves that assist the user to hold or manipulate the delivery tool 12 with a single hand. As explained herein, the housing 14 further includes the operational components of the delivery tool 12 that is used to guide placement of the delivery tool 12 to the proper anatomical location as well as deliver the implant 10 into the target tissue of nasal valve.

Figure 3A:
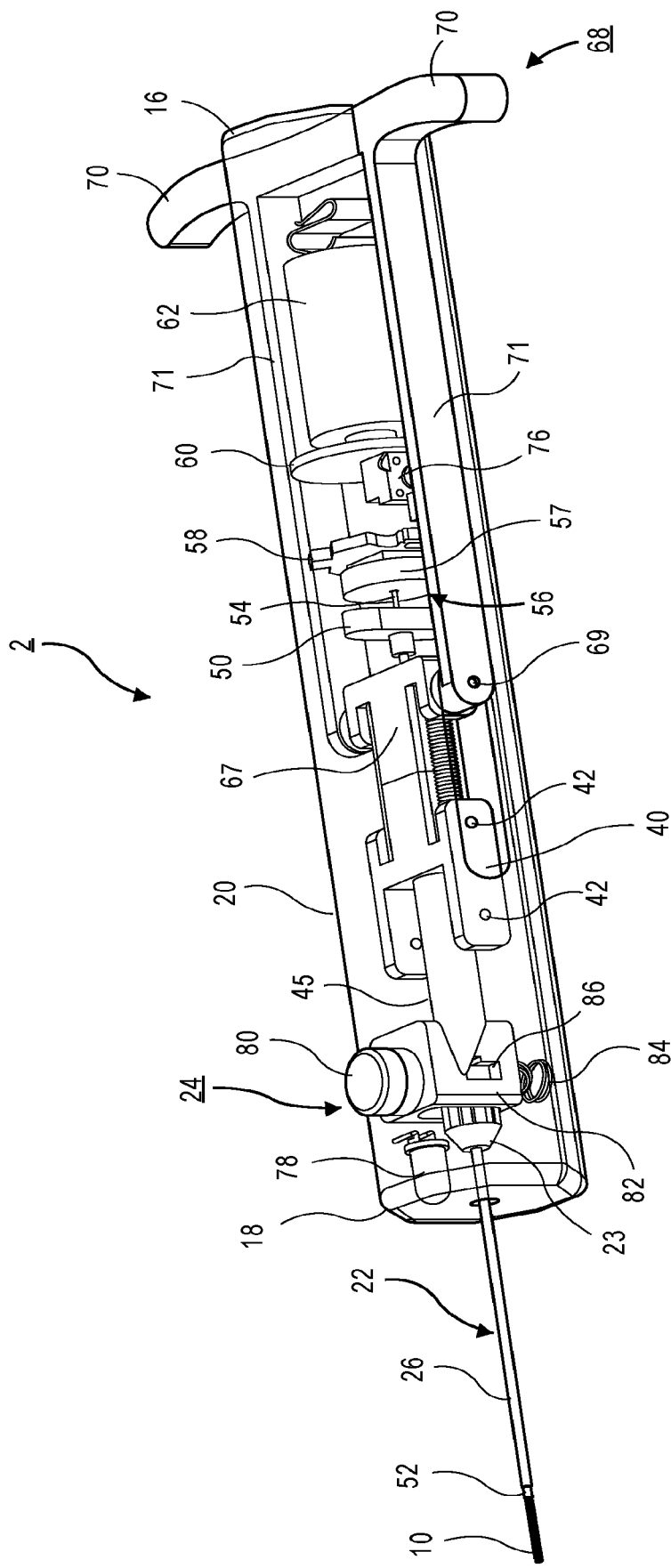
FIG. 3A illustrates a perspective view of a delivery system of FIGS. 1A and 1B after actuation of the delivery tool. The needle shuttle and needle have retracted proximally to unsheathe the implant.
Figure 3B:
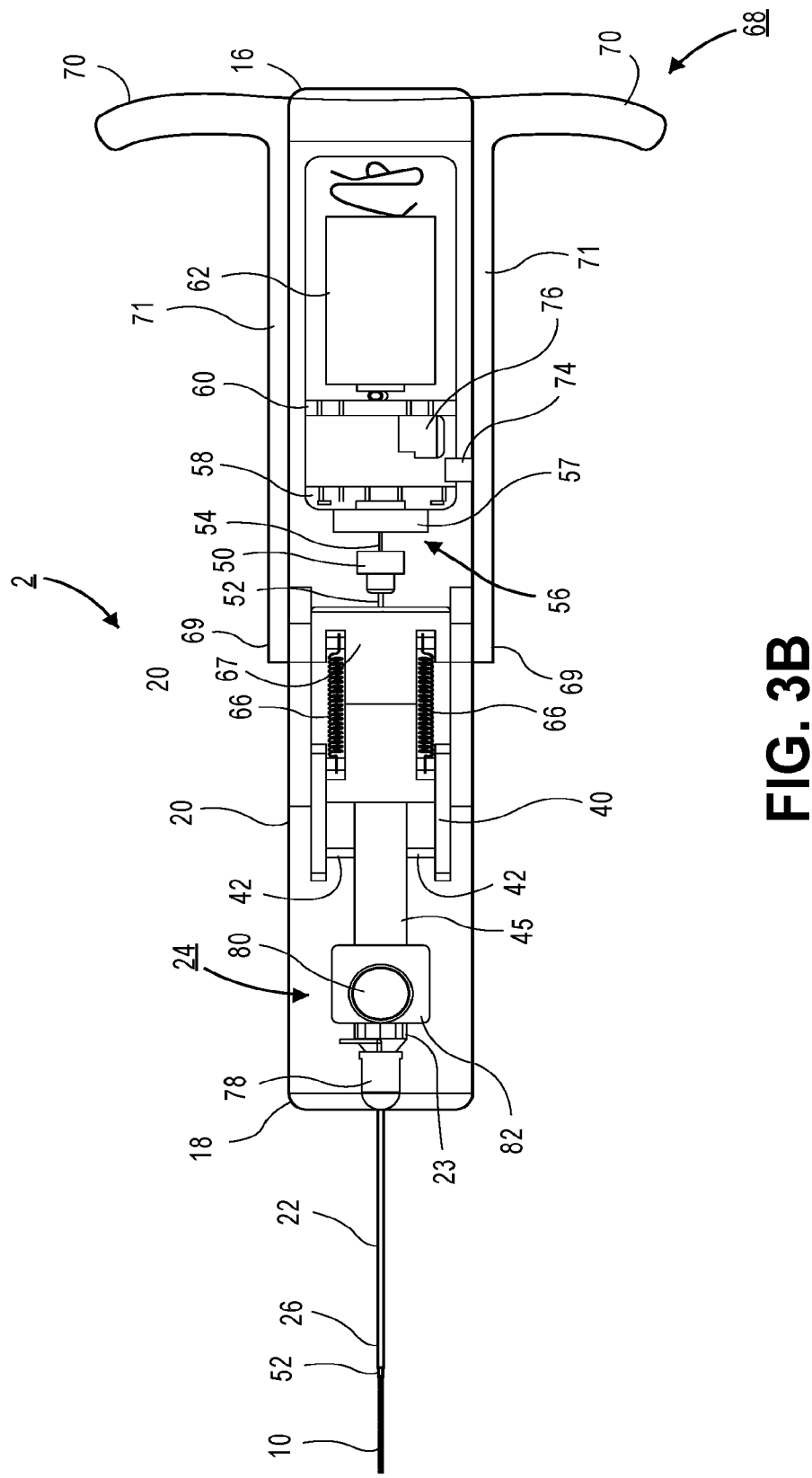
FIG. 3B illustrates a top view of the delivery system of FIG. 3A.

The distal end 18 of the handle 20 includes a needle 22 that extends distally from the distal end 18 of the handle 20. As explained herein, the needle 22 contains a hollow lumen 21 (seen in FIGS. 4B and 4C) therein that is dimensioned to receive the implant 10. In one embodiment, the needle 22 is moveable relative to the handle 20 in the direction along the long axis of the handle 20 and is moveable between an extended state (as shown, for example, in FIGS. 1A and 1B) and a retracted state (as illustrated in FIGS. 3A and 3B). In the extended state, the needle 22 contains the implant 10 in the hollow lumen as seen in FIG. 4C. The delivery tool 12, with the needle 22 in the extended state and containing the implant 10, is manipulated by the user to insert the needle 22 into the mucosal tissue of the nose of the subject near the nasal valve area. As explained in more detail below, an actuator 24 located on the delivery tool 12 is triggered by the operator (e.g., using a finger or thumb) to deploy the implant 10 from the lumen of the needle 22 in response to proximal movement of the needle 22 relative to the stationary implant 10. In this regard, the actuator 24 initiates the proximal retraction of the needle 22 at least partially into the handle 20 and thereby deploys the implant 10 from the lumen of the needle 22 in an unsheathing movement.

In a preferred embodiment, the distal tip 26 of the needle 22 is sharpened to aid in tissue penetration or tissue dissection. The needle 22 may be opaque to light (e.g., made from stainless steel or the like). Alternatively, the needle or shaft may be made from an optically transparent or translucent material. If the needle or shaft is not optically transparent or translucent, the portion of the needle 22 or shaft that extends distal of the implant 10, when the implant 10 is fully loaded in the needle 22, may be kept relatively short for safety purposes.

Figure 16A:
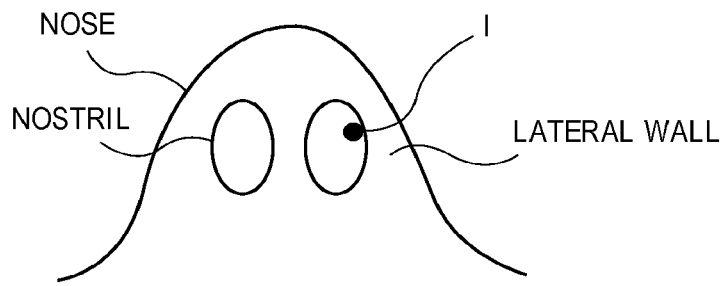
FIG. 16A illustrates a bottom view of the nose of a subject showing the nasal wall and one possible location were the needle of the delivery tool is inserted.
Figure 16B:
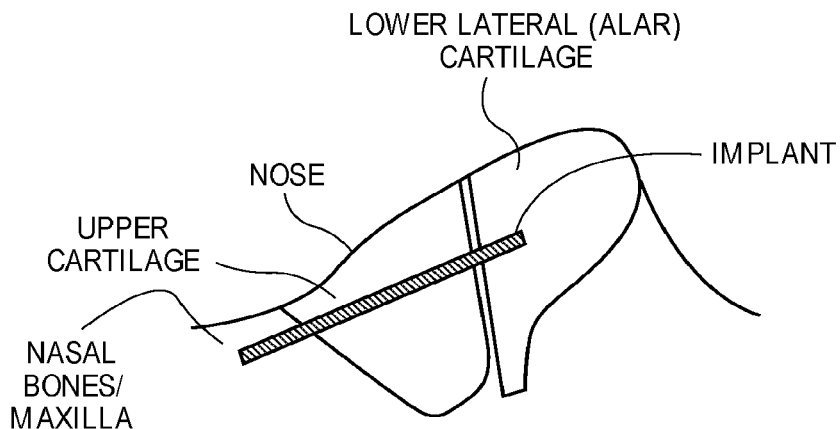
FIG. 16B illustrates a side view of the nose of the subject showing the implant deployed in the nasal valve region inside the mucosal tissue if the nose.
Figure 16C:
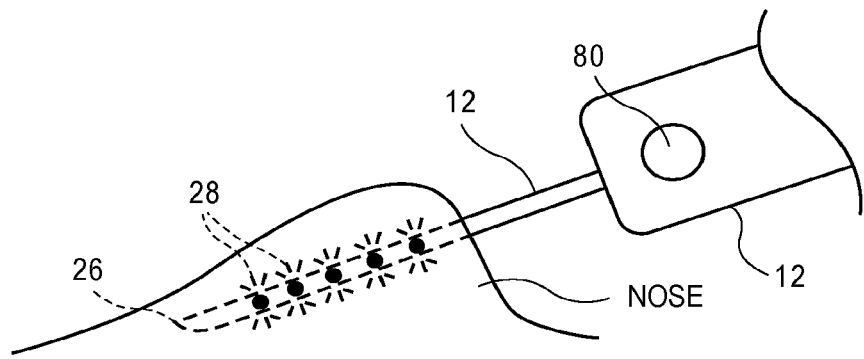
FIG. 16C illustrates light being emitted through the apertures or holes positioned along the top side of the needle of the delivery tool. This light is observable through the skin of the subject.

The needle 22 may be formed using a hollow shaft of rigid material such as, for instance, (e.g., hypotube) that terminates at a tip 26 which in some embodiments may be sharpened or beveled to aid in tissue penetration. In one embodiment, the needle 22 is 18XT gauge; although it should be appreciated that other gauges may be used. As seen in FIGS. 4D and 16C, in one embodiment, the needle 22 has holes or apertures 28 that are located in the body of the needle so that that the implant 10 may be visualized during the implantation procedure using transillumination from light that originates from a light source 56 located within (or in other embodiments passes through) the housing 14 and enters an optically transparent or translucent implant 10. In one preferred embodiment, a plurality of apertures 28 are located along a top surface of the needle 22 (that corresponds to a top surface of the handle 20) to provide visual feedback through the outside of the nose; showing the implant 10 and/or needle tip 26 location and vector of the implant 10. Light may also be emitted through a bottom surface of the needle 22 as seen in FIG. 4E via one or more apertures 28 to allow the user to visually see if the proximal end of the implant 10 is positioned fully under the nasal mucosal lining.

The apertures 28 may be equally spaced from one another as or they may have differing inter-hole distances along the length of the needle 22. The dimensions of the apertures 28 may be the same or they may differ along the length of the needle 22. For example, because light enters from one side of the needle 22, the apertures 28 located closest to that end tend to emit the brightest light. Taking this into consideration, the spacing and/or sizing of the apertures 28 may be adjusted to provide a generally uniform illumination along the entire length of the needle 22. For example, the sizes of the apertures 28 may increase as one travels along the needle 22 in the distal direction. The increasing size of the apertures 28 along the needle 22 produce a transillumination pattern that is perceived by the user as constant along the length of the needle 22. In addition or as an alternative, the needle 22 may optionally include a slotted hole near the distal tip to create a brighter zone at the tip of the needle 22.

Figure 4A:
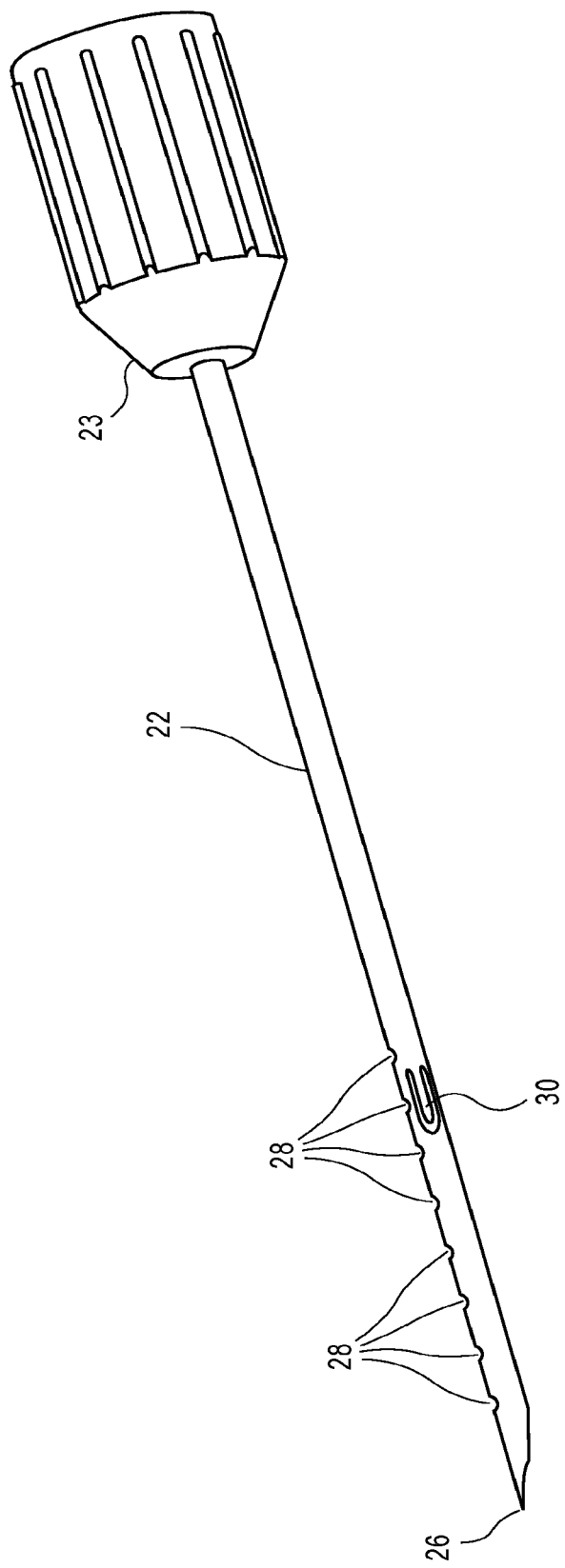
FIG. 4A illustrates a perspective view of a removable needle and hub according to one embodiment.
Figure 4B:
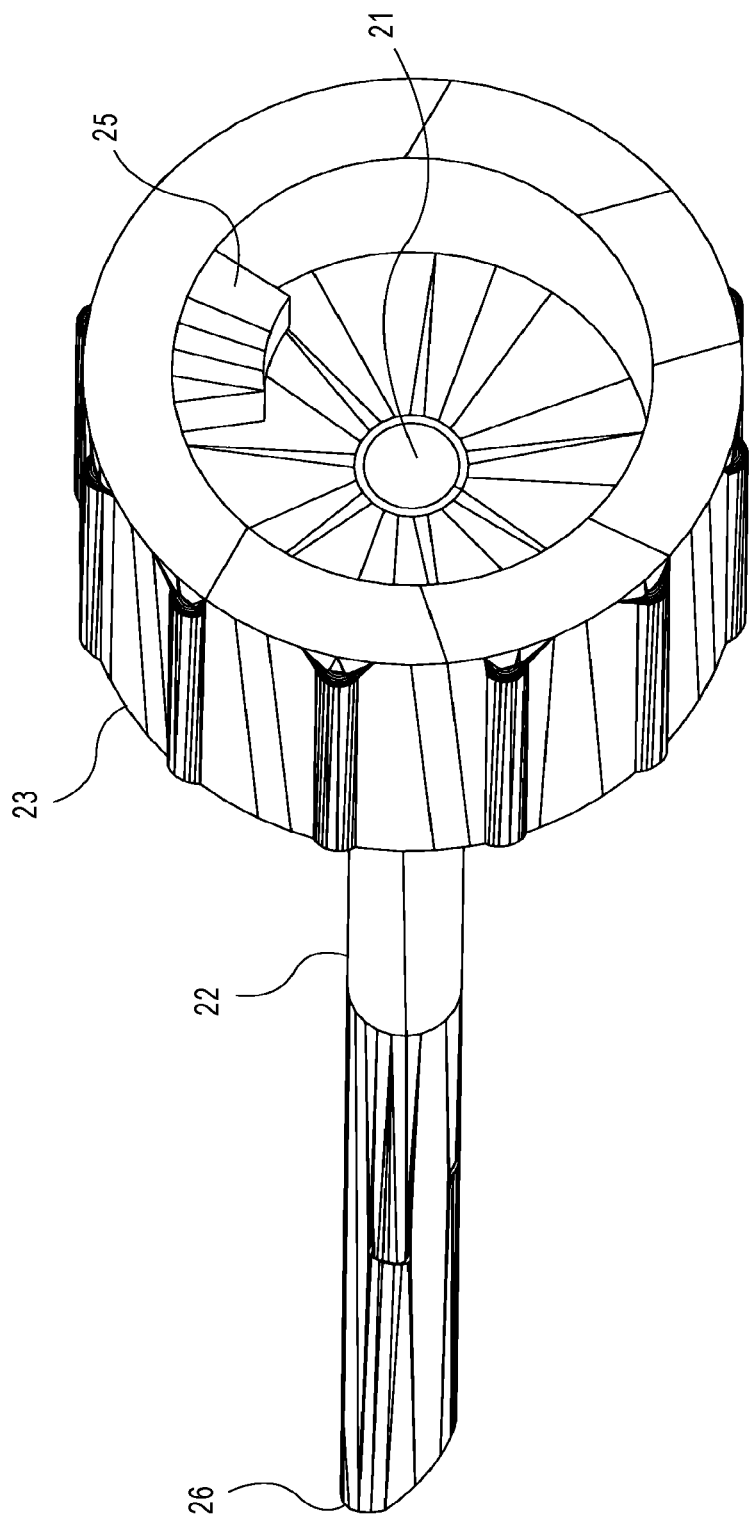
FIG. 4B illustrates another perspective view of the removable needle and hub.
Figure 4C:
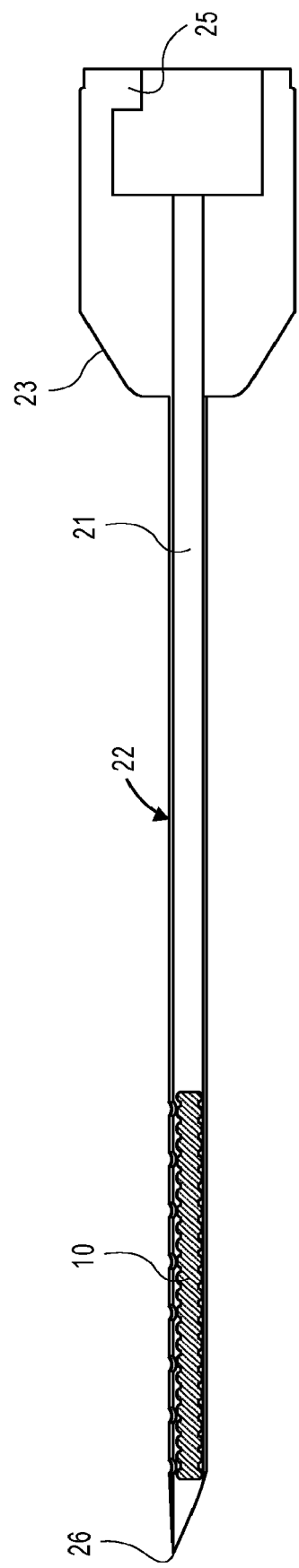
FIG. 4C illustrates a cross-sectional view of the removable needle and hub taken along the longitudinal axis of the needle. The implant is seen inside the needle.
Figure 4D:
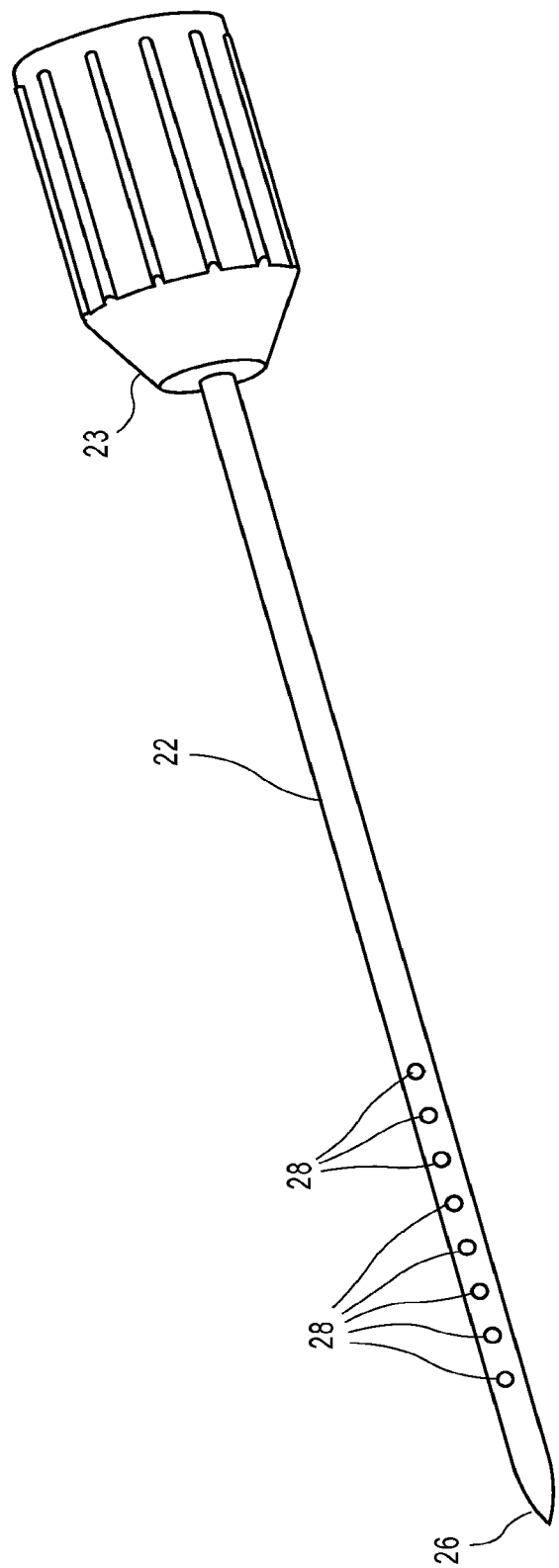
FIG. 4D illustrates another perspective view of the removable needle and hub illustrating the top surface of the needle.
Figure 4E:
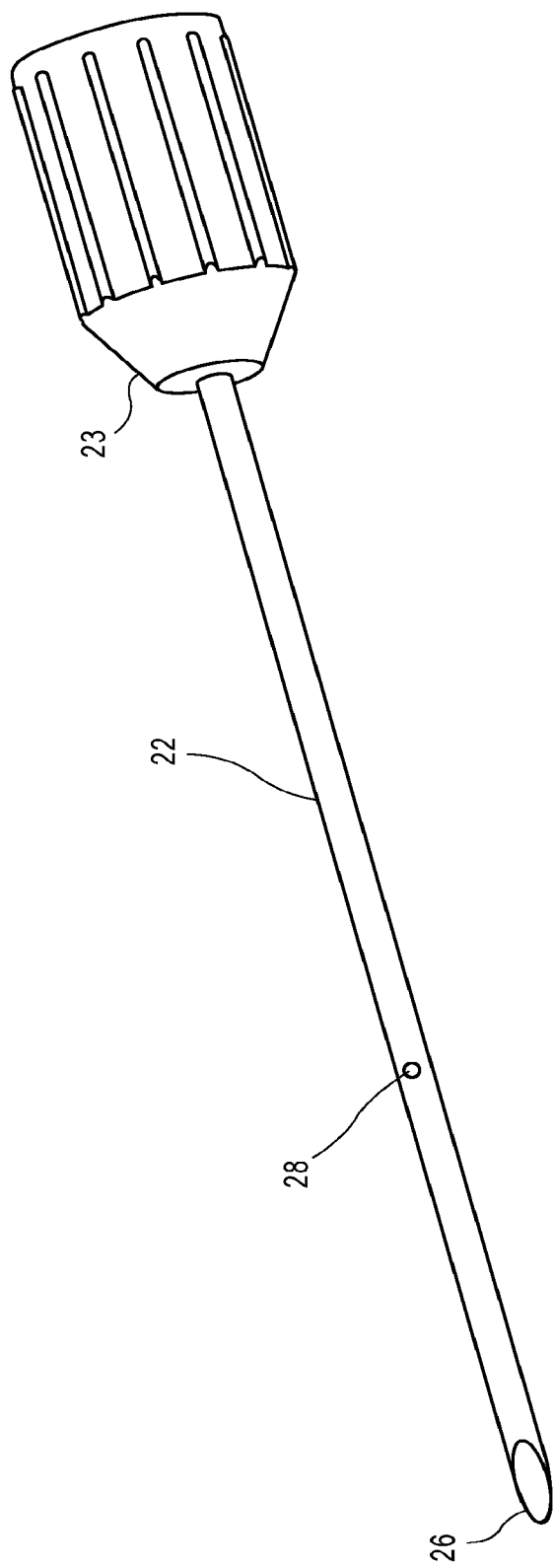
FIG. 4E illustrates another perspective view of the removable needle and hub illustrating the bottom surface of the needle.

Referring to FIG. 4A, the side of the needle 22, in one embodiment, includes partial apertures or openings that are formed or generated by respective tabs 30 that are formed in the body of the needle 22 (e.g., on opposing sides or surfaces of the needle 22) that are used to frictionally engage the implant 10 to hold the implant 10 within the needle 22 until deployment. The tabs 30 may bend inwardly toward the lumen of the needle 22 so that the tabs 30 frictionally engage the outer surface of the implant 10 to prevent premature movement or dislodgment of the implant 10 from the needle 22 until implant 10 is intentionally deployed by the operator. In some embodiments, the needle 22 includes one, two, three, four, five, six, or more than six partial apertures or openings that are formed by such tabs 30.

As seen in FIGS. 4A and 4C, in one embodiment, the tip 26 of the needle 22 is beveled such that the distal most portion of the needle 22 ends at the top surface of the needle 22 that contains the plurality of apertures 28. In this configuration, the plurality of apertures 28 on the top surface and the beveled tip 26 facing upward, towards the outer surface of the nose. By having the beveled tip 26 facing outside of the nose as illustrated allows for easier insertion into tissue (e.g., the needle 22 is less likely to skate across inner nostril surface) and also is intended to provide improved tactile feedback of contact with skull, thereby helping the user prevent undesireable contact of the tip 26 of the needle 22 with bone tissue.

Figure 5:
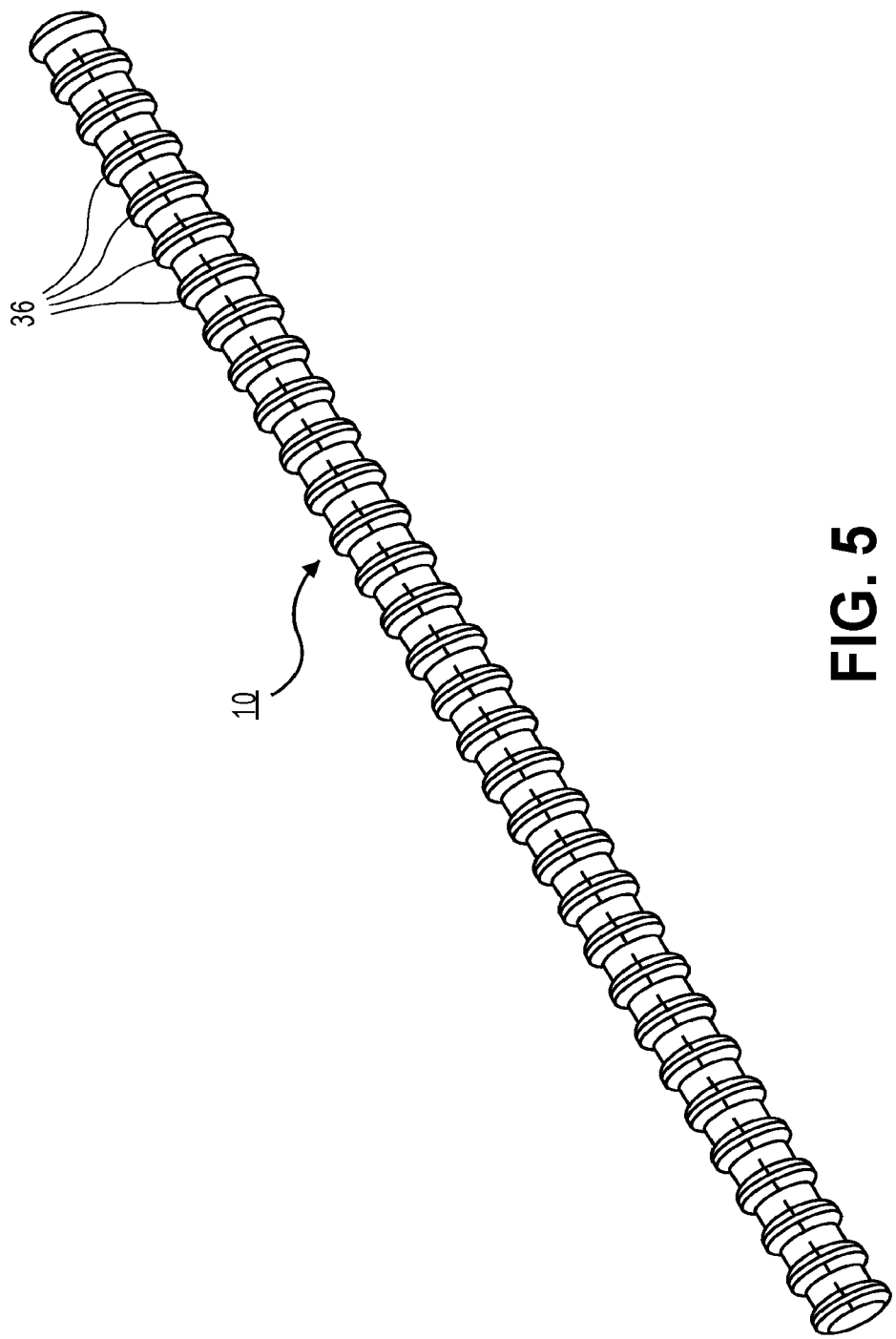
FIG. 5 illustrates a perspective view of an implant according to one embodiment.

FIG. 5 illustrates the implant 10 according to one embodiment. The implant 10 may have a variety of lengths but typically the length is within the range of about 1.5 cm to about 2.5 cm in length. Different lengths of the implant 10 may be needed depending on patient anatomy and the like. The diameter of the implant 10 may also vary and depends on the size of needle 22 that is used. The maximum outer diameter of the implant 10 should be less than the I.D. of the needle 22 so that that the implant 10 does not bind with the needle 22 during loading or deployment. A typical diameter for the implant 10 may include 0.040" or 1 mm. In some embodiments of the invention, the implant 10 may be at least partially optically translucent or optically transparent such that light is emitted from the implant 10. This provides the user with direct feedback of the orientation and positioning of the implant 10. This light may be emitted from all surfaces of the implant 10 or less than all of the surfaces of the implant 10. For example, in one optional embodiment, one or more of the external surfaces of the implant 10 may be designed to emit directional emission of light as to provide better information as to the particular orientation of the implant 10 in the underlying tissue. In some embodiments, the light is emitted only from the delivery tool 12. For example, the light may be emitted from the distal tip 26 of the needle 22. Alternatively, or in addition to the distal tip 26 of the needle 22, the light may be emitted along a length of the distal region of the needle 22 in a stripe or notch (not shown) located on one side of the needle 22 or a series of apertures 28 located in a line. In other embodiments, the light is emitted from both the delivery tool 12 and the implant 10. In still another embodiment, light is only emitted from the implant 10.

Various surfaces of the implant 10 and/or the delivery tool 12 can be patterned or texturized to provide for differing light effects. In addition, the delivery tool 12 or implant 10 may have graduation marks or the like that are illuminated by the light to reduce washout from light emitting from a larger area. In some embodiments, the implant 10 may be used to transmit light (e.g., waveguide or light transmission member). One or both of the tips of the implant 10 may, in some embodiments, be beveled, angled, or faceted to direct light in a directional fashion. In addition, the implant 10 may, in some embodiments, have a stripe along an outer surface for directional orientation.

Using the implant 10 as the light transmission member provides certain benefits. For example, if the tip of the implant 10 (or area near the tip) and/or a stripe along the implant 10, or a series of apertures 28 facing the patient's skin were to emit light, the physician could visualize where the implant 10 is located in the patient's anatomy. The lighted tip would provide an exact understanding of the implant tip location, and the stripe would provide an exact understanding of implant trajectory and orientation. The light is of sufficient intensity such that it passes through the skin or other tissue of the subject and can be visualized by the operator of the delivery tool 12 (e.g., physician). In this regard, transdermal illumination or visualization of light through the skin is used to track and monitor the positioning and/or trajectory of the delivery tool 12 and/or implant 10. In some embodiments, the ambient light may need to be turned down or reduced so that the emitted light may be observed however this may not be needed depending on the brightness of the light that is used. While FIGS. 1A, 1B, 2A, 2B, 3A, 3B illustrates the light source 56 being located inside the delivery tool 12 it should be appreciated that in other embodiments, an external light source (not shown) may be coupled to the delivery tool 12 (via light port or the like located in the handle 20) to provide the light source 56. The light that is emitted by the light source 56 is visible light, preferably red light, which better transmits through the skin of the subject.

In one embodiment, the implant 10 is made from a biocompatible polymer material that is optically transparent or translucent. The implant 10 may be made from a resorbable polymer that breaks down over an extended period of time (e.g., 12+ months). An example of a resorbable, translucent polymer is a blend of poly(l-lactic acid) (PLLA) and poly(ε-caprolactone) (PCL) (e.g., blend of 90-95% PLLA and 10-5% PCL). The implant 10 is typically rigid or semi-rigid in construction so that it resists or prevents the collapse of the nasal valve area. The implant 10 may be decorated or have various optional surface features that permit the same to be securely retained in position in the nasal valve area. These include ribs, hooks, barbs, retaining members, and the like. Optionally, the implant 10 may be loaded with one or more biologic or drug agents (e.g., an anti-inflammatory, antibiotic, or other active pharmaceutical agent).

Figure 6:
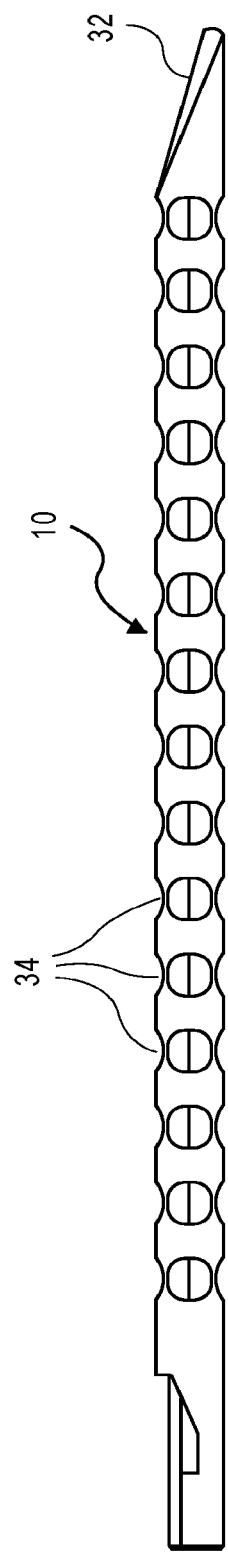
FIG. 6 illustrates a perspective view of an implant according to another embodiment.
Figure 7:
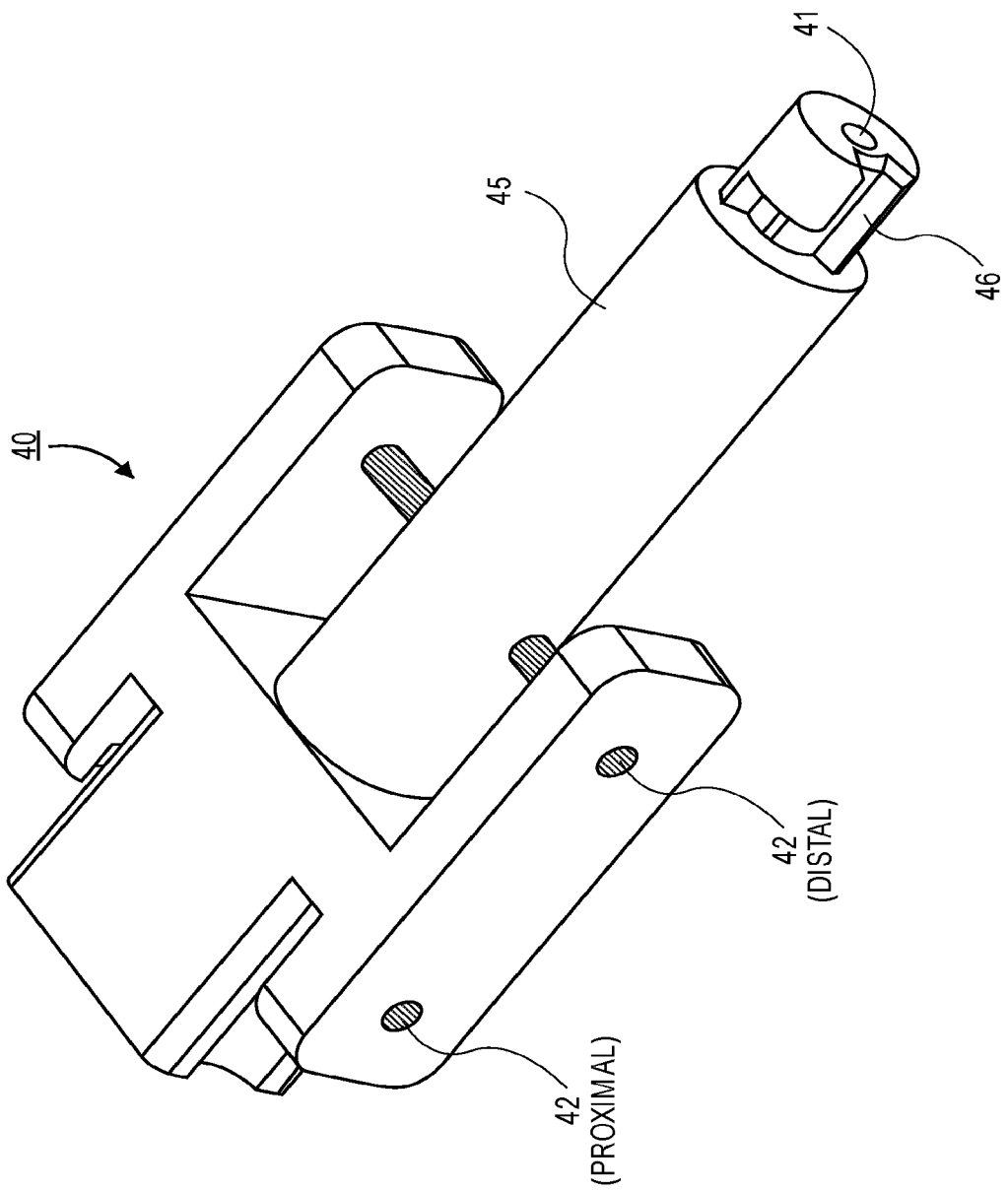
FIG. 7 illustrates a perspective view of a needle shuttle according to one embodiment. In this embodiment, the needle shuttle is secured to a needle mount that is used to mount/un-mount a removable needle.

In one embodiment, as seen in FIG. 6, the implant 10 may include a distal tip 32 that is beveled like the beveled tip 26 of the needle 22 to ease insertion of the implant 10 into tissue. However, in other embodiments, the implant 10 does not include any sort of beveled tip 26 and may be longitudinally and/or axially symmetrical, for example, as seen in FIG. 5. Another optional feature for the implant 10 includes indentations 34 located along the exterior surface of the implant 10. The indentations 34 may be, for example, circular in shape and add texture to hold the implant 10 in position after release. In addition, the indentations 34 help broadcast light out of the apertures 28 contained in the needle 22. In other embodiments, the indentations 34 may be omitted entirely. In yet another alternative embodiment as illustrated in FIG. 5, the implant 10 includes a plurality of circumferential ribs 36 that are positioned along the exterior surface of the implant 10. The ribs 36 advantageously interface with the tabs 30 of the needle 22 to aid in securing the implant 10 within the needle 22 prior to delivery. In addition, the ribs 36 serve to retain the implant 10 within the tissue of the nasal valve area after deployment.

Figure 15:
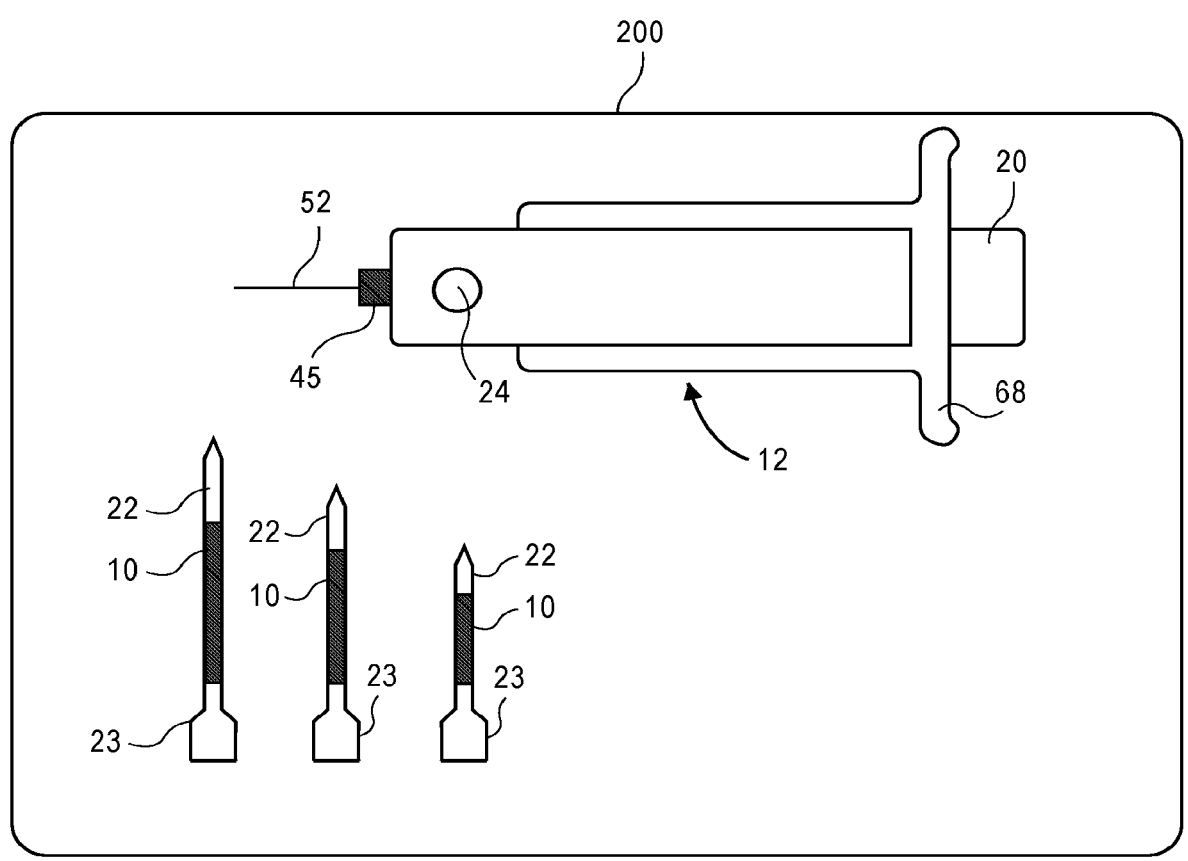
FIG. 15 illustrates one example of a kit that includes the delivery tool as well as a plurality of needles containing implants therein.

The dimensions of the implant 10 may vary depending on the point of application and the subject's anatomy. In one example, the implant 10 is cylindrical in shape and has a diameter of about 0.038 inches (~0.97 mm) and a length of around 0.79 inches (~20.07 mm). It should be appreciated that other diameters and lengths for the implant 10 may be used. In one embodiment, the implant 10 comes pre-loaded inside the needle 22. As explained herein, in one embodiment, the needle 22 may be removable with respect to the delivery tool 12. In this regard, a kit or the like (e.g., as seen in FIG. 15) may be provided to the user that includes a single delivery tool 12 along with multiple different needles 22 preloaded with implants 10. For example, there may be different lengths of implants 10 and needles 22 that are included as part of the kit. In another embodiment, the implant 10 is loaded into the needle 22 by the user. This loading of the needle 22 may require a specialized needle loading device as described herein in more detail.

With reference to FIGS. 1A, 1B, 2A, 2B, 3A, 3B, and 7, the proximal end of the needle 22 is coupled to a needle shuttle 40. The needle shuttle 40, as explained herein is used to pull the needle 22 proximally upon actuation of the delivery tool 12. The needle shuttle 40 disposed in the handle 20 rides along longitudinal tracks located in the interior of the housing 14. The needle shuttle 40 includes a plurality of proximal and distal pins or boss elements 42. The proximally located pins or boss elements 42 secure the needle shuttle 40 to a pair of springs 66 as described in more detail below. The distally located pins or boss elements 42 secure a needle mount 45 (best seen in FIG. 7) to the needle shuttle 40. Pins or boss elements 42 are also used to releasably connect shuttle actuator 24 to the needle shuttle 40. The needle mount 45 permits the needle 22 to be removably mounted via a hub 23 located on the needle 22. The hub 23 includes a boss or tooth 25 (seen in FIG. 4B) that engages with a recess 46 contained in the needle mount 45. The recess 46 enables the hub 23 to be pushed onto the needle mount 45 and rotated about a quarter turn to lock the hub 23 relative to the needle shuttle 40. The needle 22 is rotated in the opposing direction to remove the needle hub 23 from the needle mount 45. In some embodiments, the pins or boss elements 42, needle mount 45, and/or needle shuttle 40 are formed of a unitary portion of material rather than discrete pieces or components.

The needle shuttle 40 permits the needle 22 to move longitudinally in the direction of the major longitudinal axis of the handle 20. That is to say, the needle shuttle 40 and needle 22 may move distally during certain loading and arming operations of the delivery tool 12. The needle shuttle 40 and needle 22 may move proximally when the actuator 24 is actuated by the user to deploy the implant 10. In one embodiment, the needle 22 is permanently mounted to the needle shuttle 40. In an alternative embodiment, the needle 22 may be removable from the needle shuttle 40 using the hub 23 as described above. In this last configuration, different needles 22 (e.g., different length needles 22 or needles containing different implants 10) can be selectively attached to the needle shuttle 40.

With reference to FIGS. 1A, 1B, 2A, 2B, 3A, and 3C, a pusher member or anchor 48 is disposed inside the housing 14 and includes a proximal base 50 that is anchored or fixed relative to the housing 14 and a tubular element 52 that extends distally from the base 50 in the longitudinal direction. The needle shuttle 40 contains an aperture or passageway 41 (seen in FIG. 7) therein through which the tubular element 52 extends. The needle shuttle 40 thus rides over a portion of the pusher member or anchor 48. In particular, the tubular element 52 is arranged in a coaxial arrangement with the needle 22 with the tubular element 52 being located at least partially within the lumen of the needle 22 such that proximal retraction of the needle 22 moves the needle 22 proximally over the fixed tubular element 52. The outer diameter of the tubular element 52 is thus less than the inner diameter of the needle 22 so that the needle 22 can freely move relative the tubular element 52 as needed. The tubular element 52 may include a segment of hypotube that is secured to the base 50. The pusher member or anchor 48 is used during deployment of the implant 10 and prevents the implant 10 from moving proximally as the needle 22 is retracted in the proximal direction. The pusher member or anchor 48 thus acts as a proximal abutment that physically contacts the proximal end of the implant 10 while the implant 10 is unsheathed by proximal withdrawal of the needle 22.

In one embodiment, at least one optical fiber 54 is located inside the lumen of the pusher member or anchor 48 and extends along the length of the tubular element 52 and terminates at a distal end with the distal most end of the tubular element 52 (e.g., a flush arrangement between the distal end of the optical fiber 54 and the distal end of the tubular element 52). The diameter of the optical fiber 54 that is used may vary depending on the dimension of the device and pusher member or anchor 48 but is typically around 0.75 mm (~0.03 inches) or smaller in diameter. Of course, the optical fiber 54 could also be smaller or larger. As one example, the optical fiber 54 can be around 0.5 mm (~0.02 inches) in diameter or 0.75 mm (~0.03 inches) in diameter. The pusher member or anchor 48 may also be of various dimensions and may be made from, for example, a 19.5 gauge hypotube (0.039 inch OD×0.027 inch ID; 0.99 mm OD×0.69 mm ID). The pusher member or anchor 48 may be made from 19TW hypotube (0.042 inch OD×0.032 inch ID; 1.07 mm OD×0.81 mm ID) while a 0.75 mm (0.03 inches) optical fiber 54 is used for improved transdermal illumination. In yet another alternative embodiment, the optical fiber 54 could be omitted entirely and the light source incorporated into the pusher member or anchor 48.

The at least one optical fiber 54 extends proximally and is optically coupled via bezel 57 to a red colored light source 56 (e.g., red light emitting diode (LED)) mounted on an LED starboard 58 that is powered by a driver circuitry 60 that is contained in the handle 20 along with one or more batteries 62 that power the electronics and the light source 56. The red light that is emitted by the light source 56 is transmitted by the at least one optical fiber 54 down the length of the tubular element 52 where the light is end-coupled to the implant 10. The light is transmitted through the body of the implant 10 and exits via the cylindrical surface of the implant 10 and/or the implant's distal tip. The transmitted light then passes through the apertures 28 contained in the needle 22 which enables visualization of the implant 10 by the operator of the delivery tool 12. In some embodiments, the light source 56 is a laser or laser diode.

Figure 1B:
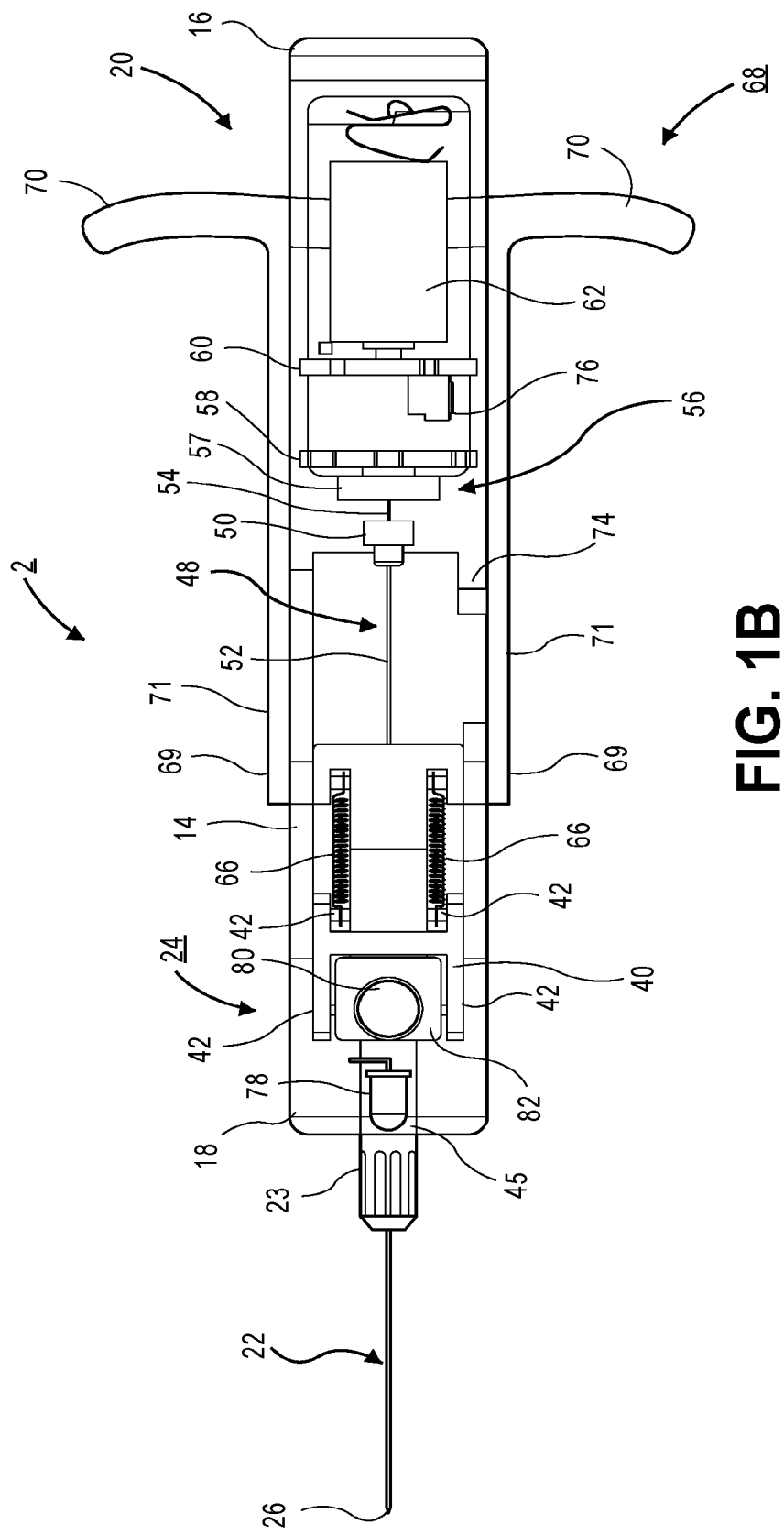
FIG. 1B illustrates a top view of the delivery system of FIG. 1A.
Figure 2A:
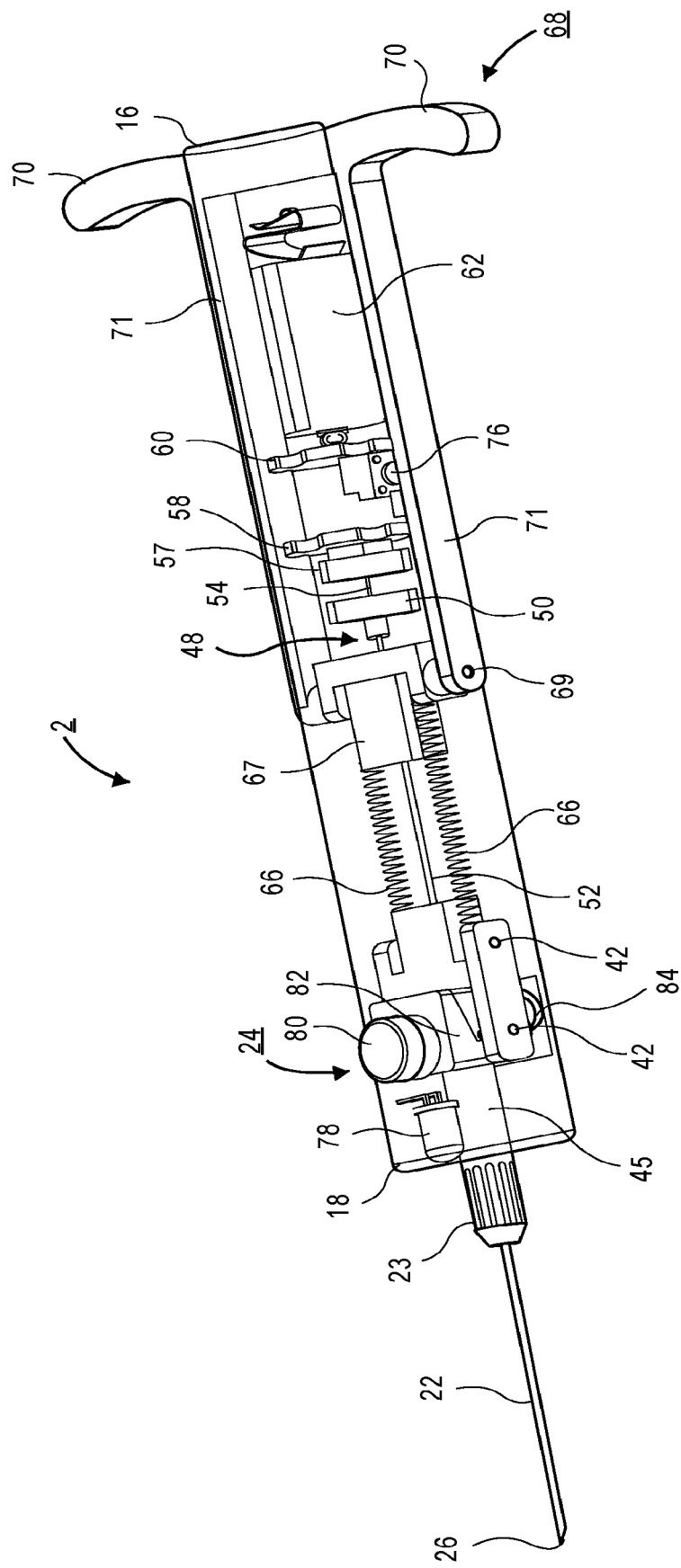
FIG. 2A illustrates a perspective view of a delivery system of FIGS. 1A and 1B with the arming lever in the armed position. The needle shuttle is under tension and locked in place via the actuator.
Figure 2B:
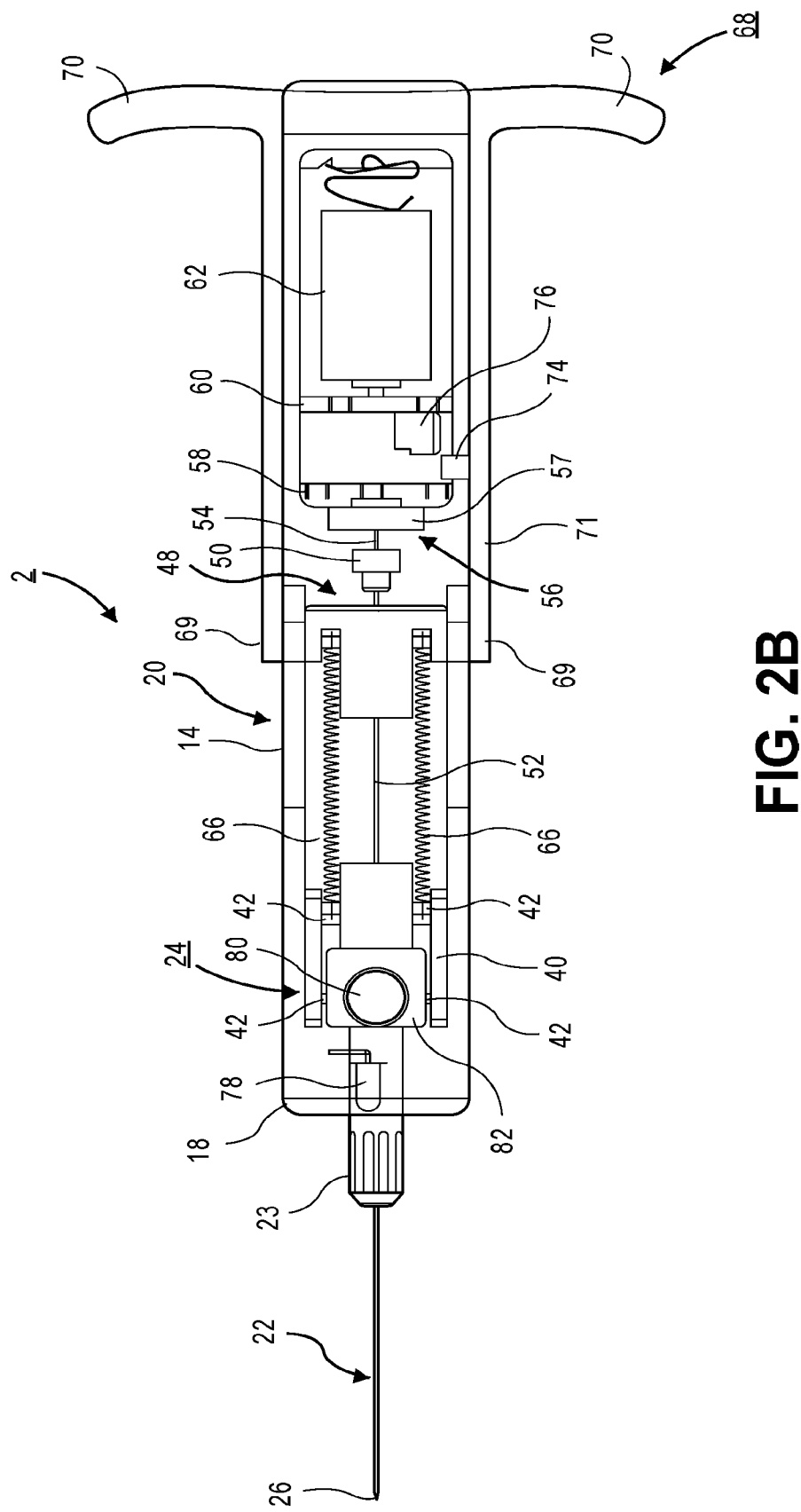
FIG. 2B illustrates a top view of the delivery system of FIG. 2A.

With reference to FIGS. 1A, 1B, 2A, 2B, 3A, 3B, the needle shuttle 40 is secured to the end of one or more springs 66 with proximal pins or bosses 42. Two such springs are illustrated in FIGS. 1B, 2B, and 3B. The opposing ends of the springs 66 are secured to an arming shuttle 67 that is coupled to a lever 68 via a pair of pins 69. The arming shuttle 67 includes an aperture therein that accommodates the tubular element 52 of the pusher member or anchor 48. The arming shuttle 67 thus slides coaxially over the tubular element 52 during the arming operation. The lever 68 is secured to the arming shuttle 67 at two side arms 71 via the pins 69 and is rotatable about pins 69 and relative to the handle 20. The lever 68 extends proximally and terminates in a pair of finger tabs 70 (other configurations are also contemplated) that are used by the operator during arming of the delivery tool 12. The arming lever 68 is used to provide a tensioning force on the needle shuttle 40 when in the armed state such that actuation of the actuator 24 will cause proximal retraction of the needle 22 and deployment of the implant 10. In one embodiment, the arming lever 68 can be locked into place to place the delivery tool 12 in armed state whereby the springs 66 are in a tensioned state. For example, the lever 68 may rest within a notch 72 that is formed in the proximal end 16 of the housing 20 that receives a cross member of the lever 68 as illustrated in FIGS. 1A and 1B. This locks the lever 68 into position and prevents the same form moving distally in response to the tensioning force of the springs 66. In an alternative embodiment, one or more locking tabs (not shown) that are disposed on an external surface of the lever 68 can be used to engage with the housing 14 to lock the arming lever 68 into position.

By utilizing an arming lever 68 that is actuated and locked into place at the point of use, this avoids placing the pair of needle retraction springs 66 in tension during sterilization and storage where there is a risk of material creep and device failure due to the stored energy deforming structural elements of the device over time. The delivery system 2 illustrated in this embodiment can be shipped with the implant 10 pre-loaded in the needle 22 with the needle 22 in the forward, locked positioned (but with the pair of retraction springs 66 not in tension). Alternatively, the implant 10 is loaded in a needle 22 that is not yet attached to the delivery tool 12. This provides for maximum ease of use for the end user. The user would open the package or kit containing the delivery system, pull the delivery tool 12 out, secure the needle 22 containing the implant 10 to the delivery tool 12 (if not already secured thereto), pull the arming lever 68 to arm the delivery tool 12, and the system is ready for immediate use.

As best seen in FIGS. 1B, 2B, and 3B, one of the arms 71 of the lever 68 includes a boss or tab 74 that extends inwardly and is positioned to actuate a switch 76 disposed in the housing 14 or on the board containing the light source driver circuitry 60 that turns on the red colored light source 56 when the arming lever 68 is pulled sufficiently proximally relative to the handle 20 and placed in the notch 72. In one embodiment, the drive circuitry 60 drives a red colored LED that is used as the light source 56 but the light source 56 may also include a red colored laser or red colored laser diode if either alternative light sources 56 are used. In one embodiment, the red colored LED of the light source 56 is turned off by removing the lever 68 from the notch 72 after the implant 10 has been deployed. In another embodiment, the LED of the light source 56 remains in an on state after being triggered and continues to operate until the battery 62 is dead. In some embodiments, the light source 56 may be actuated through use of a pull-tab (not shown) that was strategically positioned during manufacturing. The presence of the pull-tab prevent current from powering the light source 56. The user removes the pull-tab from the delivery system thereby turning the light source 56 on and the light source 56 shines continuously until the battery is dead.

In one embodiment, the switch 76 is also coupled to light source driver circuitry 60 that operates a white colored LED light 78 that is disposed at a distal end of the housing 14. The white colored light 78 assists the physician in selecting the location inside the nose where the needle would be inserted. The white colored light 78 or "headlight" that is also located in the handle may be provided by a conventional light bulb, LED or multiple LEDs that are driven by the same control board 58 used to power the red light source 56. Alternatively, a separate control board or driving circuitry located in the handle may be used to drive the white colored light 78. The white colored light 78 (e.g., LED or bulb) may be mounted at or near the distal end of the handle 20 as seen in FIGS. 1A, 1B, 2A, 2B, 3A, and 3B. The white colored light 78 may directly illuminate the target area or one or more lenses (not shown) may be contained in a lens assembly or the like that is also located in the distal end of the handle 20. Alternatively, the white colored light 78 may be located in the handle 20 (e.g., with the red LED on a common mount or circuit board) and the white light is transmitted out the distal end of the handle using a light pipe, light fiber, or bundle of fibers.

With reference to FIGS. 1A, 1B, 2A, 2B, 3A, and 3B, the actuator 24 includes a button 80 that is exposed along the surface of the handle 20 and is connected to an actuator body 82 that is spring biased against the handle 20 using a spring 84. The actuator body 82 includes notch 86 (best seen in FIG. 3A) located therein that is dimensioned to receive the distal pair of pins or bosses 42 when the needle shuttle 40 is advanced sufficiently in the distal direction. The notch 86 retains the needle shuttle 40 secured in the distally advanced position until the delivery tool 12 is fired using the button 80. Depression of the button 80 (e.g., using the thumb or finger of the same hand that holds the handle 20) moves the actuator body 82 and notch 86 so that the needle shuttle 40 is then free of the actuator body 82 and is proximally retracted into the handle 20 via the tensioned springs 66. While a notch 86 is described, it should also be understood that a pawl, latch, or the like may be used as an alternative.

FIGS. 3A and 3B illustrates the delivery tool 12 in the post-firing state with the needle 22 being proximally withdrawn at least partially into the handle 20 via the needle shuttle 40. The implant 10 that was contained inside the lumen of the needle 22 is unsheathed by the proximally retracting needle 22 and is deployed into the nasal valve area of the subject. The pusher member 48 (i.e., tubular element 52 of pusher member 48) prevents the implant 10 from proximally retracting along with the needle 22.

In the embodiment of FIGS. 1A, 1B, 2A, 2B, 3A, and 3B, there is no mechanical interlock between the pusher member or anchor and the implant which greatly reduces the possibility of dislodging the implant during removal of the delivery system. Retracting the needle 22 (rather than pushing the implant 10 out of the distal end of the needle 22) also helps prevent dislodging or misplacement of the implant 10 during delivery. In an alternative to using a pair of springs 66, the needle 22 may be actuated by other energy storage mechanisms. For example, a single spring may be sufficient to apply the needed tensioning force. An air cylinder that contains compressed air may also be used to move the needle 22 in the proximal direction. In another example, an electrically operated actuator may move the needle 22 in the proximal direction. Further, while FIGS. 1A, 1B, 2A, 2B, 3A, and 3B illustrate an embodiment in which the implant 10 is deployed by the unsheathing of the implant 10 by the proximal withdrawal of the needle 22 and the use of a pusher member or anchor 48, in an alternative embodiment, a different delivery mechanism is employed. For example, with reference to FIG. 8, another embodiment of a delivery tool 12 uses an actuator such as slide or knob 90 that is moveable (e.g., in direction of arrow A) or depressible and coupled to the needle 22. The slide or knob 90 may be slid back to release the implant 10 from the needle 22. The slide or knob 90 can be directed proximally relative to the handle 20, thereby retracting the needle 22 into the handle 20 while pusher member 92 remains stationary and holds the implant 10 static relative to the handle 20. Alternatively, the implant 10 can be unlocked from a releasable locking joint or the like.

Figure 8:
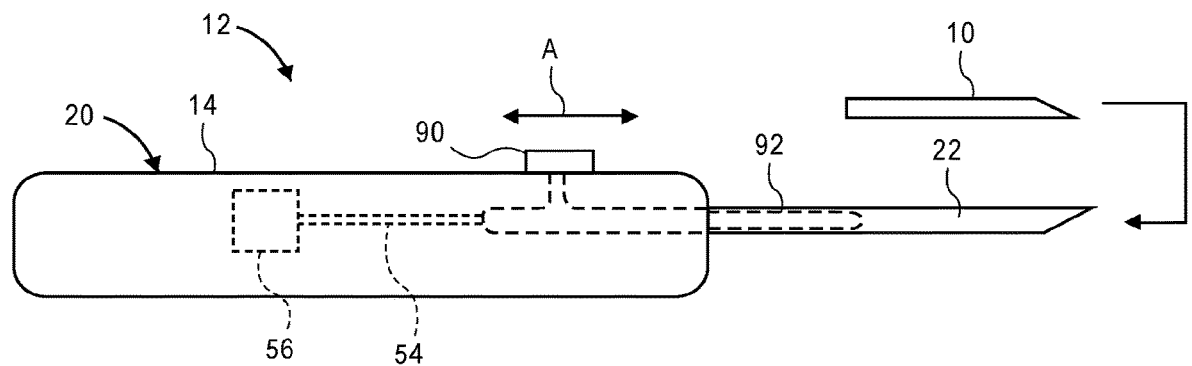
FIG. 8 schematically illustrates another embodiment of a delivery tool.
Figure 9A:
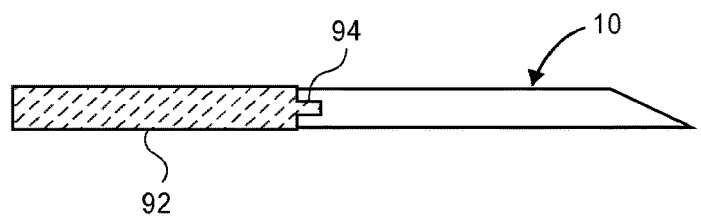
FIG. 9A illustrates one embodiment of an implant that is coupled to a distal end of a pusher member via a locking joint.
Figure 9B:
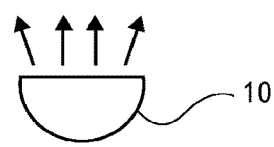
FIG. 9B illustrates a cross-sectional end view of the implant according to one embodiment.

FIG. 9A illustrates one embodiment of an implant 10 that is coupled to a distal end of a pusher member 92 via a locking joint 94. The locking joint 94 may be unlocked to release the implant 10 for deployment. The locking joint 94 may include a mechanical connection such as a clasp, interference fit, or the like. Light may be transmitted through the pusher member 92 and into the implant 10 as explained herein. The implant 10 may optionally have a flat surface on one side for directional emission of light as seen in FIG. 9B. The implant 10 could have a polished surface that is used for light emission and texture on the rest of the implant 10 or, alternatively, coated to contain internal reflection and light emission. Alternatively, light may be emitted from all of the implant 10. Note that distal tip of the implant 10 may be optionally sharpened or beveled to act as a dissection tip. FIG. 8 illustrates an embodiment of an implant 10 that is loaded or positioned in the needle 22 of a delivery tool 12. The implant 10 in this embodiment may be held in a static position by pusher member 92 while the needle 22 is retracted.

Figure 10A:
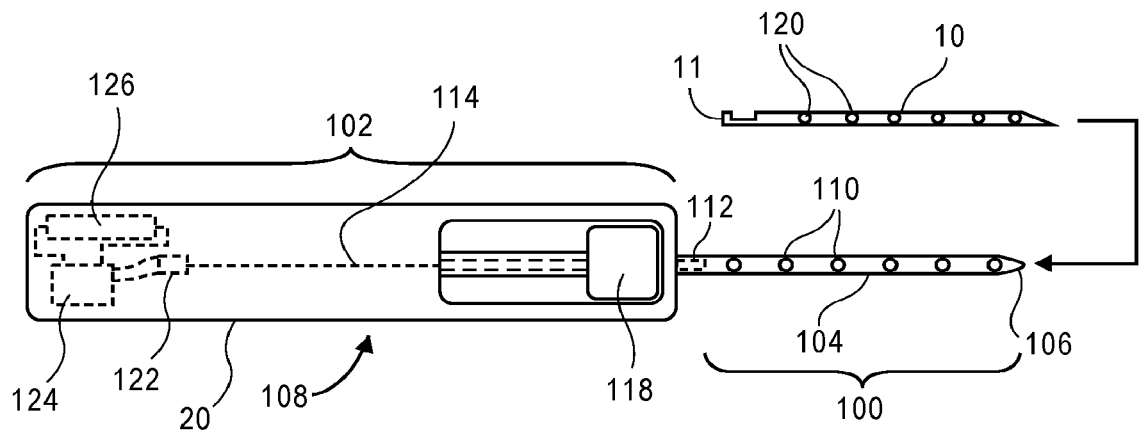
FIG. 10A illustrates a top view of another embodiment of nasal implant delivery tool.
Figure 10B:
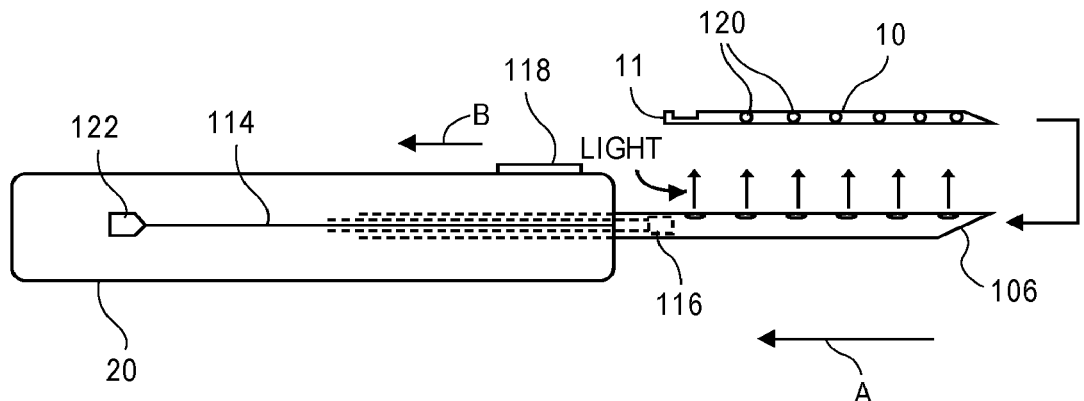
FIG. 10B illustrates a side view of the nasal implant delivery tool of FIG. 10A.
Figure 10C:
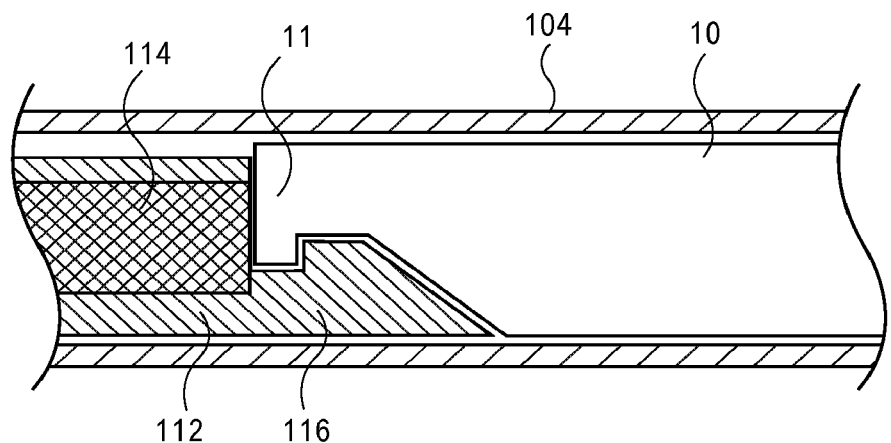
FIG. 10C illustrates a partial cross-sectional view of the nasal implant loaded onto a pusher member and contained within a shaft or needle of the implant delivery tool.

FIGS. 10A-10C illustrates another embodiment of a delivery tool 12 for delivering an implant 10 into a nasal valve area of a subject. In this embodiment, the delivery tool 12 that has a distal region 100 and a proximal region 102. The distal region 100 may include a shaft or needle 104 (e.g., hypotube) that terminates at a tip 106 which in some embodiments may be sharpened or beveled to aid in tissue penetration. In this embodiment, the beveled tip 106 is oriented with respect to the delivery tool 12 so that during use the beveled tip 106 is facing toward the outer surface of the nose. The proximal region 102 includes a handle 108 that is gripped by the user (e.g., physician) during use. In the embodiment of FIGS. 10A-10C, an implant 10 is located within the needle 104. That is to say, the implant 10 is contained within a lumen of the shaft or needle 104 that extends distally from the handle 108. The shaft or needle 104 may include 18UTS gage needle having an outer diameter (OD) of 0.050" (1.27 mm) and an inner diameter (ID) of 0.044" (1.12 mm). Of course, other sizes for the shaft or needle 104 may be used. For example, 18XX sized hypotube may also be used. In another example, the hypotube is 18XT with an OD of 0.050" (1.27 mm) and an ID of 0.042" (1.07 mm). Either needle size can accommodate a 0.040" or 1 mm diameter implant 10. In addition, as seen in FIG. 10A, holes or apertures 110 are formed in one side (e.g., top side) of the shaft or needle 104. The apertures 110 are formed on the top side of the shaft or needle 104 so that the outer surface of the nose can be illuminated as explained herein.

Still referring to FIGS. 10A-10C, the delivery tool 12 includes a pusher member 112 that partially extends into the lumen of the shaft or needle 104 and provides push support for the implant 10. In the embodiment of FIGS. 10A-10C, the pusher member 112 is stationary relative to the delivery tool 12 and the shaft or needle 104 is moveable in the proximal direction (i.e., toward the handle 108) as shown by arrow A in FIG. 10B whereby the implant 10 which is loaded into the lumen of the shaft or needle 104 is then un-sheathed and released into place. The pusher member 112 acts as a proximally-located stop that prevents proximal movement of the implant 10 as the shaft or needle 104 is retracted proximally during deployment. In one embodiment of the invention, the pusher member 112 is a 19.5 gage segment of hypotube (0.039" OD×0.027" ID; 0.991 mm OD×0.686 mm ID) that partially extends into lumen of the shaft or needle 104, although other sizes are contemplated. This size of pusher member 112 can accommodate a 0.5 mm (0.02 inch) light fiber 114. The distal end of the pusher member 112 terminates at a clasp or locking member 116 (best seen in FIG. 10C) that is used secure the proximal end of the implant 10. The proximal end of the implant 10 includes a mating clasp or locking member 11. The two clasps or locking members 11, 116 when engaged rotationally and longitudinally locks the implant 10 in place until the implant 10 is released. The pusher member 112 includes a lumen dimensioned to accommodate a light fiber 114 therein (best seen in FIG. 10C). The light fiber 114 is used to transmit light into the implant 10 for transillumination that originates from light source 122.

The implant 10 is deployable from the needle 104 of the delivery tool 12. For example, an actuator 118 such as slide, knob, or button that is moveable or slidable can be used to release the implant 10 from the delivery tool 12. In the embodiment of FIGS. 10A-10C, the implant 10 can be released from the needle 104 by a slidable button 118 that is pressed down to first unlock and then is pulled back in the proximal direction of arrow B in FIG. 10B to retract the needle 104 over the implant 10. The implant 10 is prevented from moving in the proximal direction by the pusher member 112 and is released after proximal retraction of the needle 104 over the implant 10. In an alternative construction, the actuator 118 could be connected to the pusher member 112 such that distal advancement of the actuator 118 pushes the implant 10 out of a stationary needle 104.

With reference to FIGS. 10A-10C, the light fiber 114 extends through a lumen of the pusher member 112 and terminates at or adjacent to a proximal end of the implant 10. Light that is transmitted through the light fiber 114 then enters the implant 10 wherein it exits the implant 10 radially, which may include optional the indentation features 34, as seen in FIG. 6, and out the apertures 110 of the shaft or needle 104. The proximal end of the light fiber 114 is coupled to a light source 122 such as a light emitting diode (LED) or laser diode. The light source 122 is powered by driver circuitry 124 and is powered by one or more batteries 126. In one optional aspect of the invention, the light source 122 is turned off upon retraction of the button 118. Preferably, the light source 122 emits a red light to better penetrate tissue.

To use the delivery tool 12 of the embodiment of FIGS. 10A-10C, the delivery tool 12 is advanced through nasal tissue to a desired location in the nasal valve area while light is emitted from the needle 104, wherein the light is observable through skin of the subject via transillumination. The implant 10 is then delivered to the nasal valve area by, for example pushing on the button 118 and sliding the same in the proximal direction to deploy the implant 10.

Figure 11A:
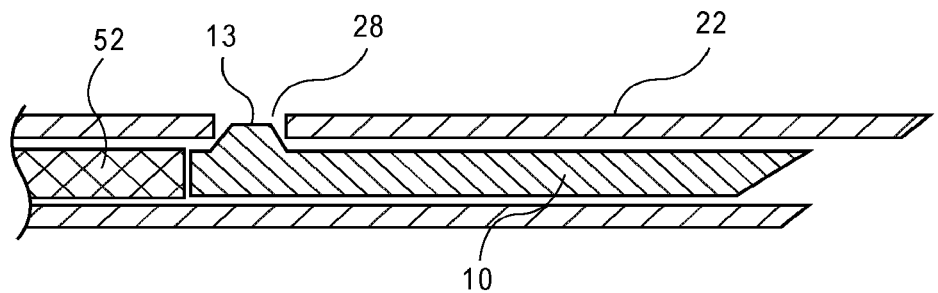
FIG. 11A illustrates a snap-fit or interference feature that is used to temporarily lock the implant into place within the needle of the delivery system.
Figure 11B:
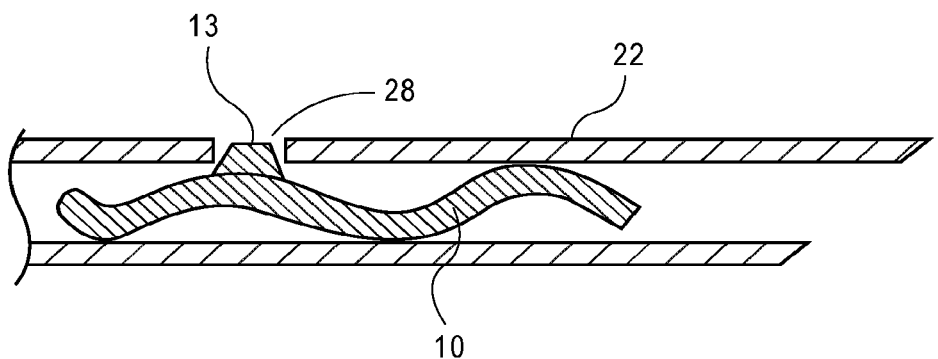
FIG. 11B illustrates another embodiment of a snap-fit or interference feature that is used to temporarily lock an implant with a spring-like shape (e.g., S-shaped or curved shape) into place within the needle of the delivery system.
Figure 11C:
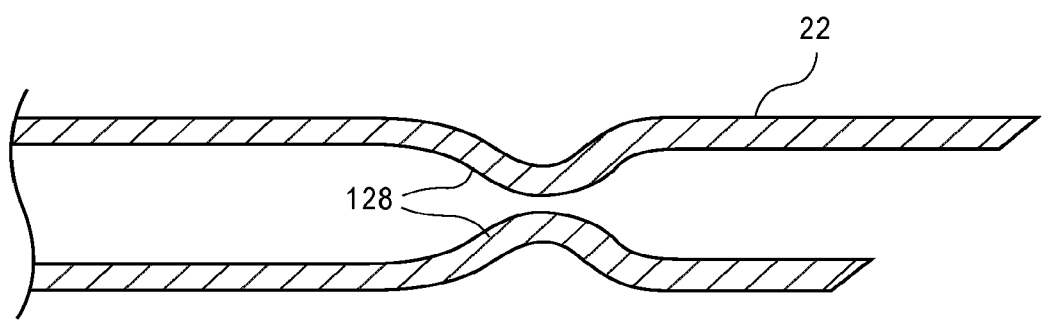
FIG. 11C illustrates a cross-sectional view of a needle having multiple tabs that are used to hold an implant according to one embodiment.
Figure 11D:
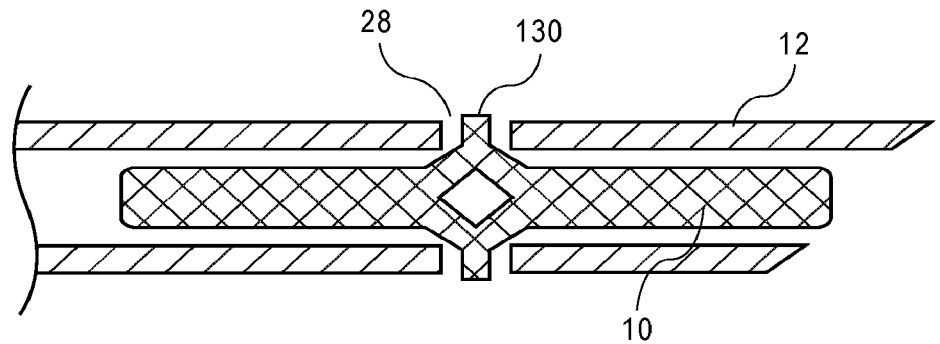
FIG. 11D illustrates a cross-sectional view of a needle having an opening or aperture that receives spring-biased tabs or arms of an implant.

FIGS. 11A-11E illustrate various embodiments of the needle 22 and implant 10 in which the needle 22 and/or the implant 10 have one or more features to temporarily engage the implant 10 with the needle 22 until deployment. FIG. 11A illustrates an implant 10 that has a protuberance or boss 13 that interfaces with a hole or aperture 28 contained in the needle. The implant 10 may "snap" into place at the desired internal location within the needle 22. The snap-fit arrangement may provide rotational alignment and hold the implant 10 in place. FIG. 11B illustrates another embodiment of a needle 22 and implant 10 whereby the implant 10 includes a protuberance or boss 13 (similar to FIG. 11A) that interfaces with an aperture 28 or slot located in the needle 22 to temporarily secure the implant with respect to the needle (e.g. snap-fit). The implant 10 may have curved shape to provide a spring-type bias to form a temporary mechanical lock between the needle 22 and the implant 10. FIG. 11C illustrates an embodiment of a needle 22 design that includes a plurality of tabs 128 (e.g., opposing tabs) that are formed in the needle 22 and are bent inward such that the implant 10 can be loaded from the distal end of the needle 22 by pushing it in and frictionally engaging with the tabs 128 to hold the implant 10 stationary with respect to the needle 22 until deployment. FIG. 11D illustrates another alternative embodiment of an implant 10 that has a spring-biased section or region 130 that interfaces with apertures or openings 28 contained in the wall of the needle 22. In still another embodiment (not illustrated), a portion of the implant 10 may be oversized to create a friction fit inside the needle.

Figure 11E:
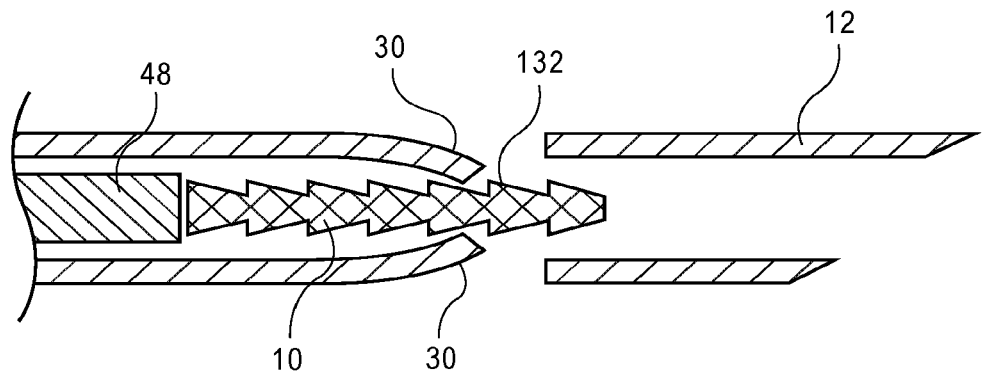
FIG. 11E illustrates a cross-sectional view of a needle having an implant therein that interfaces with tabs from the needle to temporarily hold the implant therein.

FIG. 11E illustrates yet another embodiment of temporarily locking the implant 10 to the needle 22. In this embodiment, tabs 30 located on the needle 22 engage with features 132 located on the implant 10. The tabs 30 could be formed by laser cutting the needle 22 then bending the tabs 30 inward. The tabs 30 and corresponding features 132 on the implant 10 (e.g., barbs, ribs, or the like) could be optimized for loading, needle retraction, and implant retention in tissue. An advantage of this embodiment is that it reduces the complexity of the implant 10 and allows for rotational symmetry about the long axis of the implant 10; greatly simplifying the design, production, and locating of the implant in 10 the device. In other embodiments (not illustrated), one or more tabs may be used.

The location of the interference fit or snap/tab-fit along the length of the needle 22 may be adjusted. For example, it may be desired to keep the implant 10 stabilized and affixed to the delivery system until the needle 22 is completely or mostly withdrawn. Therefore, in some embodiments, it may be advantageous to locate the features near the distal end of the needle 22. Regardless of whether the needle/implant interface is friction fit, snap-fit, tab-fit, etc., the temporary connection that is formed is overcome by the rapid proximal withdrawal of the needle 22 when the actuator 24, 118 is triggered. Such an embodiment requires less precision in manufacturing, will always release from the implant 10, and can be easily reloadable.

Using features on the needle 22 and/or implant 10 to form a temporary lock between the implant 10 and needle 22 permits the easy loading and reloading of the delivery system through the distal end of the needle 22. To load or reload the device, in one embodiment, the needle 22 is advanced distally relative to the handle 20 and locked into place. The implant 10 is then inserted into the tip of the needle 22 and seated within the needle 22. As discussed below, a loading tool or fixture may be used to assist in this process. The tool or fixture may be particularly useful for loading implants 10 that do not have rotational symmetry.

The tool or fixture provides the additional safety benefit of reducing needle stick injuries during the loading/reloading process.

Figure 12:
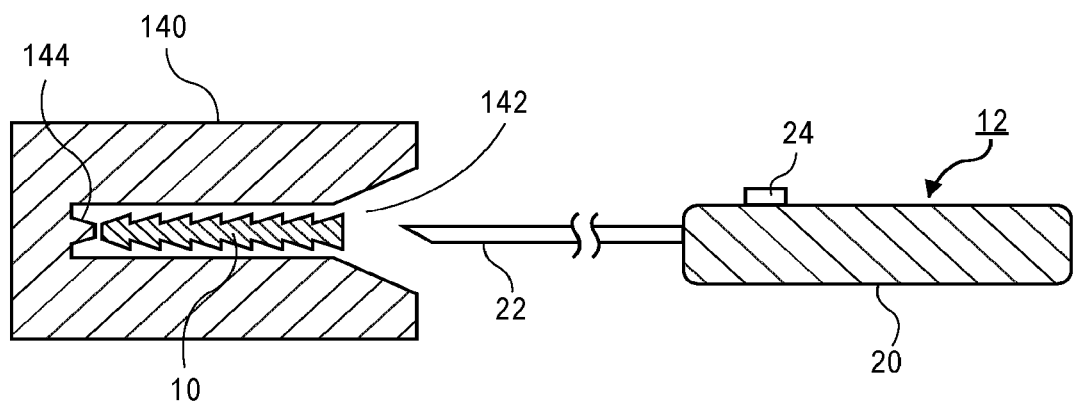
FIG. 12 illustrates one embodiment of a nasal wall implant loading/reloading tool.

FIG. 12 illustrates one embodiment of an implant loading/reloading tool 140. The tool 140 is used to house the implant 10 which can then be loaded into the distal end of the needle 22. In one embodiment, the tool 140 or fixture may be pre-loaded with the implant 10 which can then be loaded into the delivery tool 12 by the user. Alternatively, the delivery tool 12 may be pre-loaded with an implant 10 and the tool 140 or fixture is pre-loaded with a second implant 10 which can be quickly loaded by the user into the delivery tool 12 as needed. In yet another alternative, each implant 10 is preloaded in the tool 140 (or multiple tools) (or the user loads the tool 140 with the implant 10) and the physician loads the needle 22 with the implant 10 from the tool 140. As seen in FIG. 12, the tool 140 includes the implant 10 disposed in a recess or cavity 142 in a forward-facing arrangement. An abutment 144 located in the tool 140 acts as a distal stop and prevents distal movement of implant 10 during the loading/reloading operation. To load the needle 22 with the implant 10 the user inserts the needle 22 into the recess or cavity 142 which guides the needle 22 over the implant 10. The needle 22 is advanced further until the implant 10 is secured in place (e.g., through snap-fit, tab-fit arrangement). Alternatively, the recess is dimensioned such that the needle 22 is pushed all the way until the needle 22 cannot advance any further.

Figure 13A:
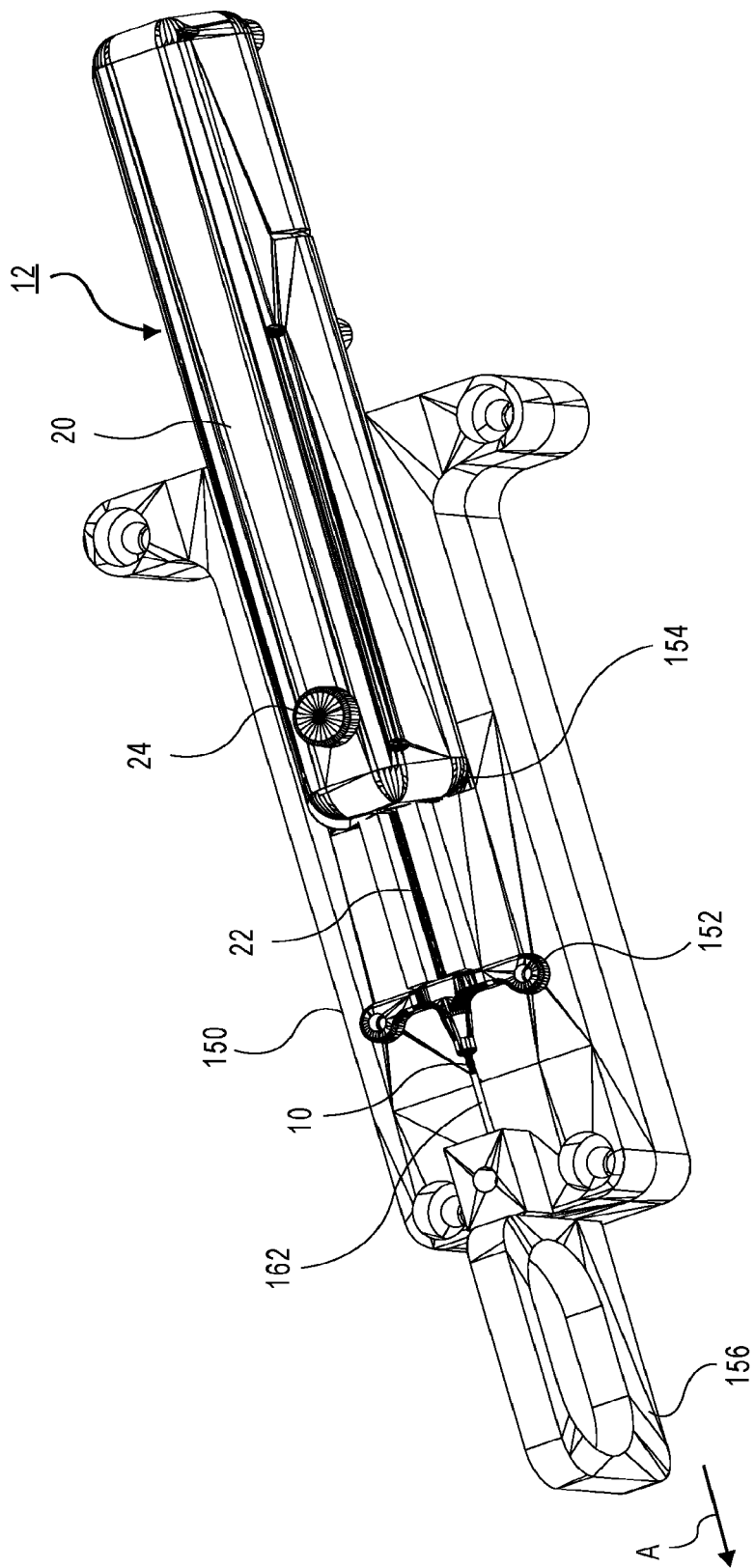
FIG. 13A illustrates another embodiment of an implant loading/reloading tool. The implant loading tool is pre-loaded with an implant loaded therein.
Figure 13B:
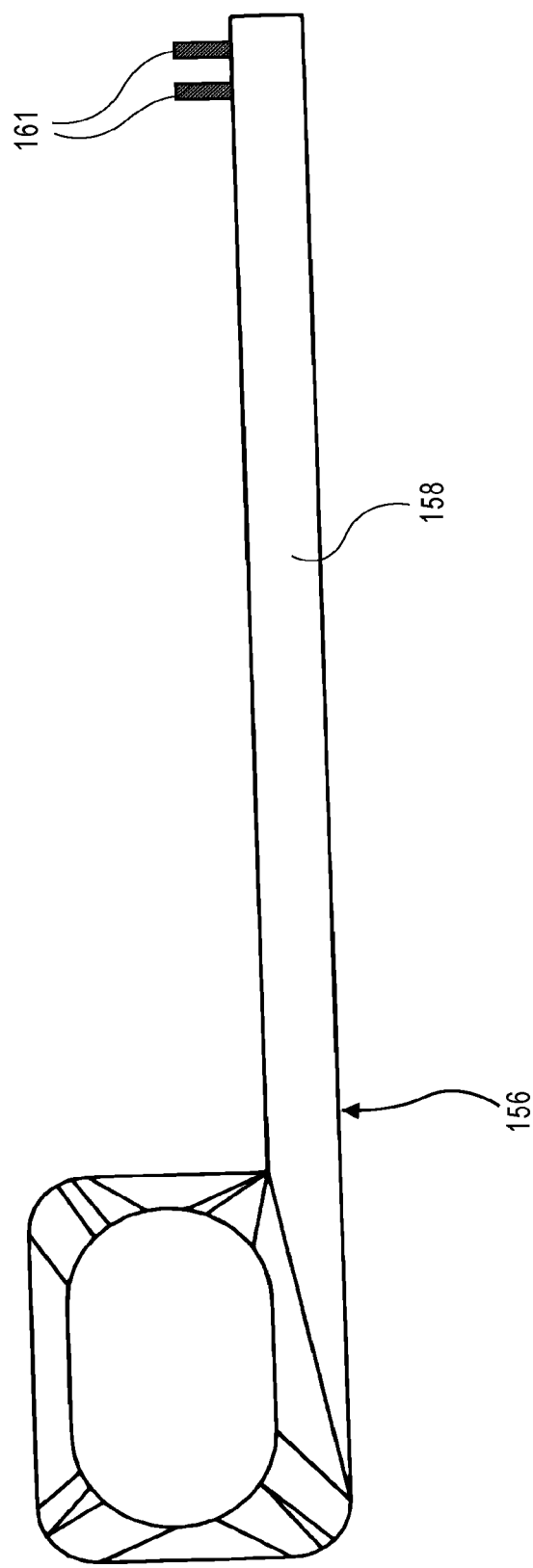
FIG. 13B illustrates a side view of the actuation lever.
Figure 13C:
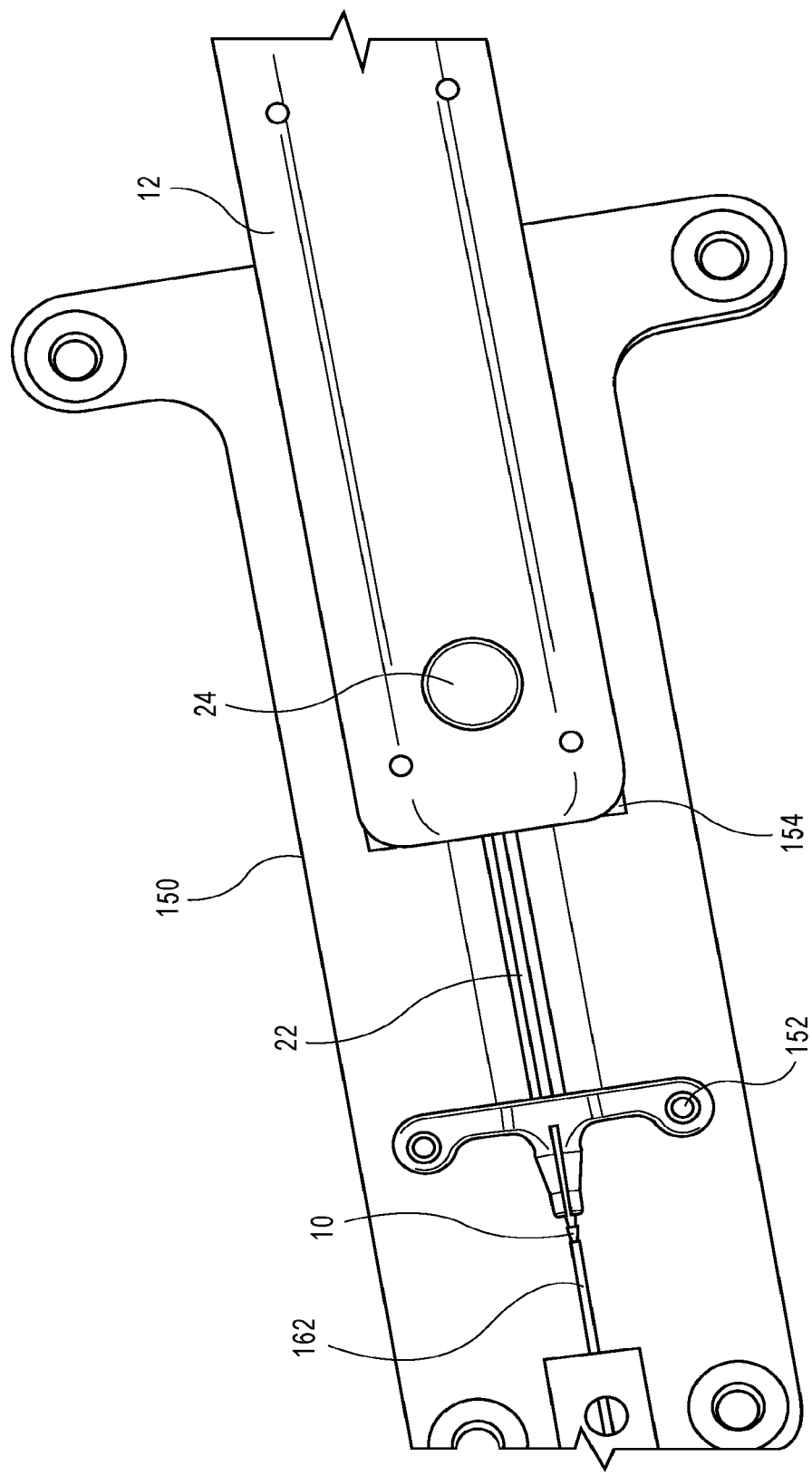
FIG. 13C illustrates a magnified view showing the implant located in the collet. The delivery system is loaded into the recess of the implant loading/reloading tool.

FIGS. 13A-13C illustrate another embodiment of an implant loading/reloading tool 150 with the implant loading tool 150 being pre-loaded with an implant 10 loaded therein. The implant 10 is secured to the loading tool via a collet 152. The implant loading tool 150 includes a recess 154 into which the delivery tool 12 is placed to load the implant (FIGS. 13A and 13C). Specifically, the delivery tool 12 with the needle (and springs 66 relaxed) in the retracted position is inserted into the recess 154 of the implant loading tool 150. To load the implant 10 into the delivery tool 12, a lever 156 is pulled back in the direction of arrow A in FIG. 13A to automatically extend the needle 22 distally with respect to the handle 20 and lock the needle 22 in the forward position and load the implant 10 in the needle 22. FIG. 13B illustrates the lever 156 which includes an extension 158 that ends with a pair of pins 161. These pins 161 engage with the needle shuttle 40 located inside the delivery tool. Movement of the needle shuttle 40 causes corresponding movement of the needle 22 as explained herein.

Referring to FIGS. 13A and 13C, a pin 162 is set in the loading tool 150 along the axial path defined by the implant 10 and the needle 22 and prevents axial movement of the implant 10 while the needle 22 is advanced over the implant 10 by actuation of the lever 156. The delivery tool 12 is then removed from the implant loading tool and is ready for use.

Figure 14A:
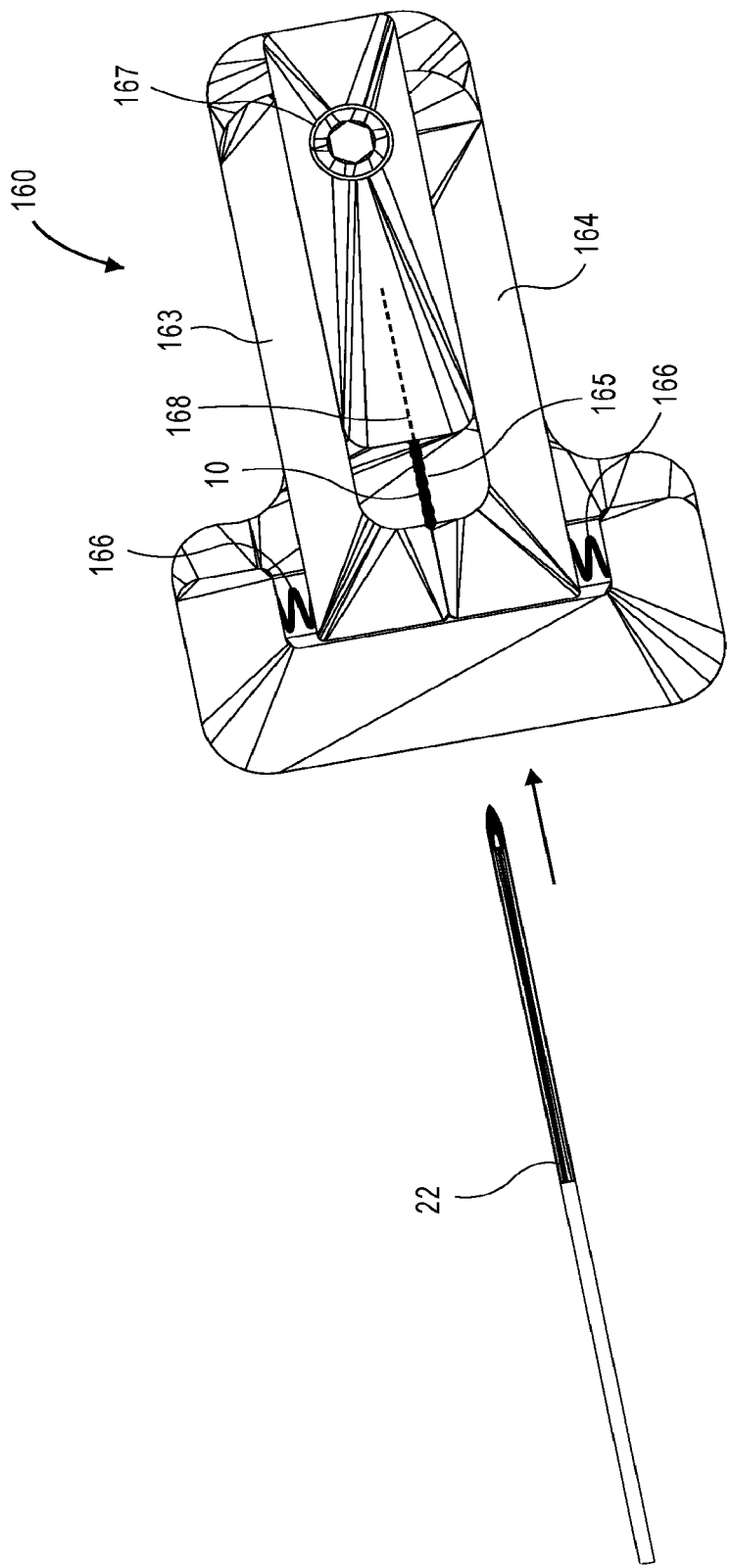
FIG. 14A illustrates a perspective view of another embodiment of an implant loading/reloading tool. The needle of the delivery tool has not yet been inserted into the tool.
Figure 14B:
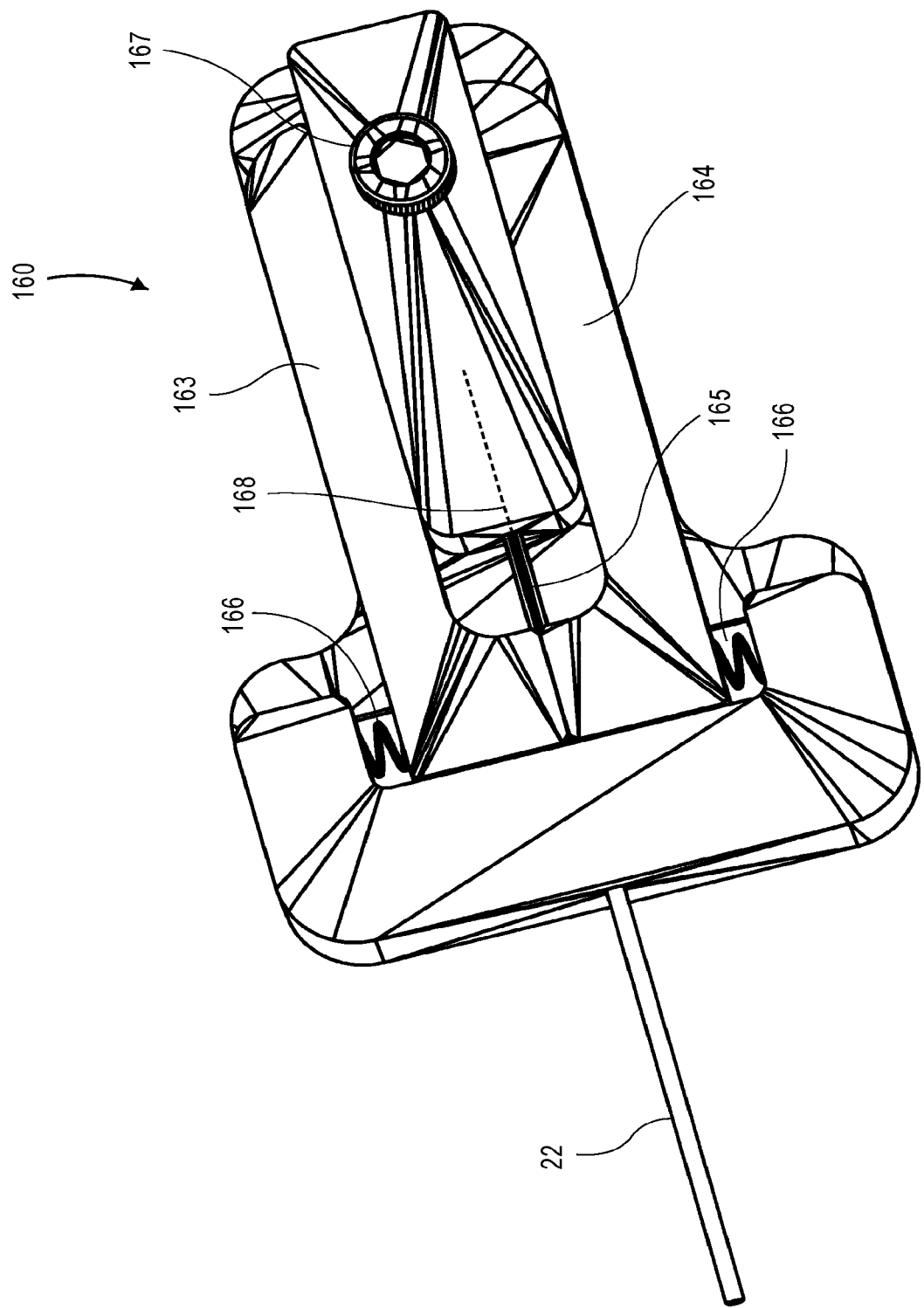
FIG. 14B illustrates a perspective view of the implant loading/reloading tool of FIG. 14A where the needle of the delivery tool has been inserted into the tool.

FIGS. 14A and 14B illustrates another embodiment of an implant loading tool 160. In this embodiment, the tool 160 includes two implant grips 163, 164 that are rotatably mounted on a fastener 167 that are spring biased by respective springs 166 to grab opposing sides of the implant 10. A needle alignment track 165 is formed in the implant loading tool 160 and is dimensioned and aligned to receive the needle 22 of the delivery tool 12. A pin 168 is located in the implant loading tool 160 and abuts one end of the implant 10 to hold the implant 10 in place. To load the implant 10, a user inserts the needle 22 of the delivery tool 12 into the needle alignment track 165 and advances the same. The needle alignment track 165 is aligned coaxially with respect to the implant 10 so that advancement of the needle 22 in the needle alignment track 165 advances the needle 22 over the stationary implant 10. The needle 22 is advanced until the implant 10 "locks" to the needle 22 one of the temporary securement measures described herein (e.g., snap-fit, tab-fit, etc.). The two implant grips 163, 164 separate as the needle 22 is advanced over the implant 10. The implant 10 is prevented from moving with the needle 22 due to the pin 168. Once the implant 10 locks into the place, the needle 22 (with implant 10) can be removed from the implant loading tool 160.

It should be understood that the implant loading tools 140, 150, 160 described herein are optional. As explained previously, in another embodiment as illustrated in FIG. 15, a kit 200 may be supplied that includes the delivery tool 12 as explained herein along with a plurality of needles 22 that have been pre-loaded with implants 10. For example, there may be provided different length needles 22 having identical or different implants 10. Alternatively, needles 22 of the same length may be provided with different implants 10. For example, implants 10 of different length or physical construction may be provided in the needles 22. This way, the practitioner can use the particular needle 22/implant 10 set that best suits the particular patient's need.

To use the delivery systems 2 described herein, such as the delivery tool 12 illustrated in FIGS. 1A, 1B, 2A, 2B, 3A, and 3B, the patient or subject is given anesthesia prior to the implantation procedure. If the procedure is done in an office setting as an outpatient procedure, the patient may be given a combination of topical and injectable anesthetics. In addition, prior to the procedure, the patient may be prescribed anti-anxiety medication that is taken prior to arriving at the office. Of course, the procedure may also take place in a hospital or other clinical environment such as an operating room. In such instances, the patient may be given a general anesthetic instead of a local anesthetic. During the procedure, the patient is typically lying on his or her back in a flat or slightly elevated position if under general anesthetic. If the patient is awake, he/she may be positioned in an upright or reclined sitting position.

With the patient prepared for implantation, the physician plans the position of the implant within the patient's nose. As part of this process the physician may mark the external surface of the nose with one or more marks (e.g., using a surgical pen) to aid in planning the target implantation location and trajectory. If not already done, the physician then, for example, loads a needle 22 (e.g., from kit 200) that contains the implant 10 onto the delivery device 12. The delivery device 12 is then armed by proximal pulling of the arming lever 68 as described herein. This arming operation turns on the red colored light source 56 as well as the white colored light 78. If the delivery device 12 includes a pull tab, the physician or an assistant may remove it to actuate the light source(s) 56, 78 or other electrical components of device 12.

The delivery device 12 is then used to establish a pathway within the nasal tissue for the implant 10. Typically, the needle 22 is advanced into the nasal mucosa of the lateral wall of the nasal cavity near the nasal opening. FIG. 16A illustrates the general location (I) where the needle 22 is inserted into the nasal mucosa. The needle 22 is advanced through the middle thickness of the lateral wall with care taken so as to avoid piercing through either the nasal mucosa or the outer skin of the nose. Note that during this process, transillumination may be used to monitor the progress of the insertion of the needle 22 into the lateral wall of the nose. The depth of penetration of the needle 22 may vary but typically the implant 10 is placed across both the upper lateral cartilage and the lower lateral (Alar) cartilage as seen in FIG. 16B. The delivery device 12 is oriented to place the holes or apertures 28 on the top surface of the needle 22 outwardly so that the transilluminated light may be observed by the physician to confirm the proper trajectory and advancement of the needle 22 as seen in FIG. 16C. In addition, the physician will also look inside the patient's nostril to confirm the location using the single aperture 28 located on the bottom surface of the needle 22. Once the needle 22 (and implant 10) is confirmed to be in the desired location, the physician will activate the actuator 24 (e.g., depress button 80 with the thumb) which will cause the rapid proximal retraction of the needle 22, leaving the implant 10 in place. The delivery tool 12 can then be removed from the nasal region. Optionally, a second or more implants 10 may be placed into the anatomy before the delivery tool 12 is removed from the nasal region or after re-inserting the delivery tool 12 into the nasal region.

Depending on the operation, the delivery tool 12 may then be used again to perform the same process in the patient's other nasal passage. The same delivery tool 12 can be used whereby another needle 22 containing the implant 10 is loaded onto the delivery tool 12 and the same process described above is repeated for the other side of the patient's nose. Of course, in some situations, only a single implant 10 is placed one of the patient's nasal passage. In addition, the operation described above may be performed in conjunction with other nasal operations. These include, by way of example, inferior turbinate reduction, septalplasty, balloon dilation of the sinus ostia or sinus passageways, or the like.

While the invention has been described herein as using a delivery tool 12 that is used to both prepare the tissue for implantation as perform implantation, another method would be to use the delivery tool 12 to first prepare a "pocket" in the tissue surrounding the desired implantation site followed by delivery of the implant 10. Pocket preparation could be done by blunt dissection of tissue planes, needle insertion, or cutting out a core of tissue. Once the pocket is ready, a separate delivery tool could be used to place the implant into the prepared pocket. In addition, while the invention has principally been described in the context of delivering an implant 10 into a nasal valve area of a subject, tools with a light emitting tip and/or stripe could be useful for other surgical techniques. Blunt dissecting instruments used, for example, for cosmetic surgery, liposuction tools, etc. could all be made easier to use by adding light guidance.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. An implant delivery system for delivering an implant into a nasal valve area, the implant delivery system comprising:
   a housing comprising a handle having a proximal end and a distal end, wherein a longitudinal axis extends in a direction between the proximal end and the distal end of the handle;
   a needle extending from the distal end of the handle, wherein the needle is movable relative to the handle along the longitudinal axis of the handle;
   a pusher member disposed in a lumen of the needle and non-removably coupled to the housing;
   a moveable needle shuttle disposed in the handle and coupled to the needle;
   one or more springs coupled to the moveable needle shuttle, wherein the one or more springs are configured to apply a proximal tensioning force on the moveable needle shuttle; and
   an actuator configured to releasably engage with the moveable needle shuttle,
   wherein the actuator is configured to be actuated to release the moveable needle shuttle from the actuator such that the moveable needle shuttle moves the needle proximally relative to the housing, which (i) retracts the needle at least partially into the handle, and (ii) deploys the implant from a distal tip of the needle,
   wherein the pusher member is configured to prevent proximal movement of the implant while the moveable needle shuttle moves the needle proximally to deploy the implant from the distal tip of the needle.

2. The implant delivery system of claim 1, further comprising an arming lever disposed in the handle and coupled to the one or more springs,
   wherein the arming lever is configured to move proximally relative to the handle to extend the one or more springs and apply the proximal tensioning force on the moveable needle shuttle.

3. The implant delivery system of claim 1, wherein the moveable needle shuttle is configured to move along a plurality of longitudinal tracks in an interior of the handle.

4. The implant delivery system of claim 1, wherein the moveable needle shuttle comprises one or more pins that are coupled to the one or more springs.

5. The implant delivery system of claim 4, wherein the one or more pins comprises a first pin on a first side of the moveable needle shuttle and a second pin a second side of the moveable needle shuttle, and
   wherein the one or more springs comprises a first spring coupled to the first pin and a second spring coupled to the second pin.

6. The implant delivery system of claim 5, further comprising an arming shuttle, wherein the first spring is further coupled to the arming shuttle and the second spring is further coupled to the arming shuttle.

7. The implant delivery system of claim 6, further comprising an arming lever coupled to the arming shuttle, wherein the arming lever is configured to be locked in an armed position in which the one or more springs apply proximal tensioning force on the moveable needle shuttle.

8. The implant delivery system of claim 7, wherein the arming lever comprises a plurality of finger tabs extending laterally from the arming lever.

9. The implant delivery system of claim 7, wherein the arming lever is configured to couple to a notch on the handle to lock the arming lever in the armed position.

10. The implant delivery system of claim 1, wherein the actuator comprises a notch that is configured to receive at least one of a pin or a boss of the moveable needle shuttle when the moveable needle shuttle is in a distal position relative to the handle, and
   wherein the actuator is configured such that actuation of the actuator releases the at least one of the pin or the boss from the notch to allow the moveable needle shuttle to move in response to the proximal tensioning force applied to the moveable needle shuttle by the one or more springs.

11. The implant delivery system of claim 1, wherein the needle is movable between an extended state and a retracted state,
   wherein, in the extended state, the needle contains the implant, and
   wherein, in the retracted state, the implant is deployed from the needle.

12. The implant delivery system of claim 11, wherein the needle comprises a plurality of tabs that are configured to frictionally engage the implant and hold the implant within the needle until the needle is moved to the retracted state.

13. The implant delivery system of claim 12, wherein the implant comprises a plurality of ribs circumferentially disposed on the implant.

14. The implant delivery system of claim 1, wherein a distal tip of the needle is beveled.

15. The implant delivery system of claim 1, wherein the actuator is coupled to the moveable needle shuttle by a pin, and
   wherein actuation of the actuator releases the pin to move the moveable needle shuttle affected by the proximal tensioning force of the springs, thus retracting the needle proximally into the handle and deploys the implant.

16. The implant delivery system of claim 1, wherein the pusher member is fixedly and non-movably coupled to the handle.

17. The implant delivery system of claim 1, wherein the actuator comprises a button on the handle.

18. The implant delivery system of claim 1, wherein the needle is removably coupled to the moveable needle shuttle, and
   wherein the needle comprises a proximal hub that is secured to the moveable needle shuttle via a needle mount.

19. The implant delivery system of claim 1, wherein the moveable needle shuttle comprises an aperture that defines a passageway through the moveable needle shuttle, and
   wherein the pusher member extends through the passageway in the moveable needle shuttle such that the moveable needle shuttle is moveable along the pusher member.

20. The implant delivery system of claim 1, wherein, after the moveable needle shuttle moves the needle proximally a first time, the moveable needle shuttle is configured to be rearmed such that the one or more springs reapply the proximal tensioning force on the moveable needle shuttle.

* * * * *

UNITED STATES PATENT AND TRADEMARK OFFICE
CERTIFICATE OF CORRECTION

| | | |
|---|---|---|
| PATENT NO. | : 11,931,071 B2 | Page 1 of 1 |
| APPLICATION NO. | : 17/214875 | |
| DATED | : March 19, 2024 | |
| INVENTOR(S) | : Andrew T. Forsberg and Anthony A. Duda | |

It is certified that error appears in the above-identified patent and that said Letters Patent is hereby corrected as shown below:

On the Title Page

On page 2, item (60) should correctly appear as follows:
Provisional application No. 62/456,427, filed on Feb. 8, 2017, provisional application No. 62/417,210, filed on Nov. 3, 2016, provisional application No. 62/378,577, filed on Aug. 23, 2016, provisional application No. 62/330,439, filed on May 2, 2016.

Signed and Sealed this
Fifth Day of November, 2024

Katherine Kelly Vidal
*Director of the United States Patent and Trademark Office*